United States Patent
Saito et al.

(10) Patent No.: US 10,345,515 B2
(45) Date of Patent: Jul. 9, 2019

(54) BONDED STRUCTURE, METHOD FOR MANUFACTURING THE SAME, AND BONDING STATE DETECTION METHOD

(71) Applicants: MITSUBISHI HEAVY INDUSTRIES, LTD., Tokyo (JP); The University of Tokyo, Tokyo (JP)

(72) Inventors: Nozomi Saito, Tokyo (JP); Takayuki Shimizu, Tokyo (JP); Toshio Abe, Tokyo (JP); Shu Minakuchi, Tokyo (JP); Nobuo Takeda, Tokyo (JP); Yutaka Terada, Tokyo (JP)

(73) Assignees: MITSUBISHI HEAVY INDUSTRIES, LTD., Tokyo (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 15/537,543

(22) PCT Filed: Jan. 6, 2016

(86) PCT No.: PCT/JP2016/050229
§ 371 (c)(1),
(2) Date: Jun. 19, 2017

(87) PCT Pub. No.: WO2016/114194
PCT Pub. Date: Jul. 21, 2016

(65) Prior Publication Data
US 2017/0341340 A1    Nov. 30, 2017

(30) Foreign Application Priority Data
Jan. 15, 2015    (JP) .................................. 2015-005748

(51) Int. Cl.
*B32B 7/12*    (2006.01)
*B32B 3/28*    (2006.01)
(Continued)

(52) U.S. Cl.
CPC .............. *G02B 6/022* (2013.01); *B32B 3/085* (2013.01); *B32B 3/263* (2013.01); *B32B 3/28* (2013.01);
(Continued)

(58) Field of Classification Search
CPC .. G01D 5/353; G01D 5/3537; G01D 5/35374; C09J 5/00; G01L 1/24;
(Continued)

(56) References Cited

U.S. PATENT DOCUMENTS

| 5,015,842 A | 5/1991 | Fradenburgh et al. |
| 5,281,388 A | 1/1994 | Palmer et al. |

(Continued)

FOREIGN PATENT DOCUMENTS

| CN | 1202964 | 12/1998 |
| CN | 102841052 | 12/2012 |

(Continued)

OTHER PUBLICATIONS

Office Action dated Nov. 14, 2017 in U.S. Appl. No. 14/784,600.
(Continued)

*Primary Examiner* — Michael P Mooney
(74) *Attorney, Agent, or Firm* — Wenderoth, Lind & Ponack, L.L.P.

(57) ABSTRACT

The purpose of the present invention is to provide a bonded structure, a method for manufacturing the same, and a bonding state detection method which are capable of determining whether or not members are bonded together appropriately. A bonded structure 10 includes a laminated sheet 12A, a laminated sheet 12B, an adhesive 14 that bonds the laminated sheet 12A and the laminated sheet 12B together, and a distributed optical fiber 16 sandwiched between the laminated sheet 12A and the laminated sheet 12B. The
(Continued)

cross-sectional shape of the distributed optical fiber 16 is deformed in accordance with the bonding state.

18 Claims, 19 Drawing Sheets

(51) Int. Cl.

| | | |
|---|---|---|
| *B32B 3/26* | (2006.01) | |
| *B32B 3/08* | (2006.01) | |
| *B32B 9/00* | (2006.01) | |
| *B32B 9/04* | (2006.01) | |
| *C09J 5/00* | (2006.01) | |
| *G01L 1/24* | (2006.01) | |
| *B32B 15/08* | (2006.01) | |
| *B32B 15/20* | (2006.01) | |
| *B32B 27/06* | (2006.01) | |
| *G01M 11/08* | (2006.01) | |
| *G01N 19/04* | (2006.01) | |
| *G01N 33/44* | (2006.01) | |
| *G02B 6/02* | (2006.01) | |
| *G02B 6/34* | (2006.01) | |

(52) U.S. Cl.
CPC ............ *B32B 7/12* (2013.01); *B32B 9/007* (2013.01); *B32B 9/045* (2013.01); *B32B 15/08* (2013.01); *B32B 15/20* (2013.01); *B32B 27/06* (2013.01); *C09J 5/00* (2013.01); *G01L 1/24* (2013.01); *G01L 1/242* (2013.01); *G01L 1/245* (2013.01); *G01M 11/086* (2013.01); *G01N 19/04* (2013.01); *G01N 33/44* (2013.01); *G02B 6/02076* (2013.01); *G02B 6/34* (2013.01); *B32B 2250/40* (2013.01); *B32B 2307/546* (2013.01); *B32B 2605/18* (2013.01)

(58) Field of Classification Search
CPC ........ G01L 1/242; G01N 19/04; G01N 33/44; B32B 2605/18; B32B 7/12; B32B 3/085; B32B 3/263; B32B 3/28; B32B 9/007; B32B 9/045; B32B 15/08; B32B 15/20; B32B 27/06; B32B 2250/40; B32B 2307/546; G02B 6/02076; G02B 6/022; G02B 6/34
USPC .............................................. 385/12, 13, 37
See application file for complete search history.

(56) References Cited

U.S. PATENT DOCUMENTS

| | | |
|---|---|---|
| 5,399,854 A | 3/1995 | Dunphy et al. |
| 5,469,520 A | 11/1995 | Morey et al. |
| 5,770,155 A | 6/1998 | Dunphy et al. |
| 5,828,059 A | 10/1998 | Udd |
| 6,254,215 B1 | 7/2001 | Hiroki et al. |
| 8,327,716 B2 | 12/2012 | Kreuzer et al. |
| 9,244,007 B2 | 1/2016 | Fukuzawa et al. |
| 2003/0085938 A1 | 5/2003 | Imanaka et al. |
| 2004/0206893 A1 | 10/2004 | Sato |
| 2006/0081772 A1 | 4/2006 | Williams et al. |
| 2006/0104561 A1 | 5/2006 | Ivtsenkov |
| 2012/0327401 A1 | 12/2012 | Fukuzawa et al. |
| 2014/0071454 A1 | 3/2014 | Fukuzawa et al. |
| 2016/0069793 A1* | 3/2016 | Saito ................. G01D 5/35351 73/705 |

FOREIGN PATENT DOCUMENTS

| | | |
|---|---|---|
| EP | 0 967 080 | 12/1999 |
| EP | 1 057 638 | 12/2000 |
| JP | 10-505920 | 6/1998 |
| JP | 11-300951 | 11/1999 |
| JP | 2000-501176 | 2/2000 |
| JP | 2000-79693 | 3/2000 |
| JP | 2000-343706 | 12/2000 |
| JP | 2001-296110 | 10/2001 |
| JP | 2002-219108 | 8/2002 |
| JP | 2003-57599 | 2/2003 |
| JP | 2005-164938 | 6/2005 |
| JP | 2006-352053 | 12/2006 |
| JP | 2011-17652 | 1/2011 |
| JP | 2011-185790 | 9/2011 |
| JP | 2013-7680 | 1/2013 |
| WO | 97/19325 | 5/1997 |
| WO | 98/10242 | 3/1998 |
| WO | 2014/185119 | 11/2014 |

OTHER PUBLICATIONS

International Search Report dated Mar. 22, 2016 in International (PCT) Application No. PCT/JP2016/050229 with English translation.
Written Opinion of the International Searching Authority dated Mar. 22, 2016 in International (PCT) Application No. PCT/JP2016/050229 with English translation.
International Search Report dated Jun. 3, 2014 in International (PCT) Application No. PCT/JP2014/054826 with English translation.
Written Opinion of the International Searching Authority dated Jun. 3, 2014 in International (PCT) Application No. PCT/JP2014/054826 with English translation.
Japanese Office Action dated Jul. 5, 2016 in Japanese Patent Application No. 2015-516958 with English translation.
Extended European Search Report dated Dec. 14, 2016 in European Patent Application 14797172.5.
Chinese Office Action dated Dec. 29, 2016 in Chinese Patent Application No. 201480021967.6 with English translation.
U.S. Office Action dated Jun. 6, 2017 in U.S. Appl. No. 14/784,600.
Nobuhira Tanaka, et al., "Simultaneous Measurement of Strain and Temperature Using Birefringence Effect of an FBG Sensor", Ninth Materials and Processing Conference, Nos. 01-26, The Japan Society of Mechanical Engineers, pp. 33-34, Nov. 2, 2001.
Nobuhira Tanaka, et al., "Strain Measurement by the Smart Patch Using FBG Sensors", 43rd Proceedings of the JSASS/JSME Structures Conference, The Japan Society for Aeronautical and Space Sciences, pp. 209-212, Aug. 1, 2001.
Nobuo Takeda, Shu Minakuchi, Yusaku Ito, "Recent Advances in Cure Process Modeling and Monitoring Methods of Advanced Composite Materials/Structures", Transactions of The Japan Society of Mechanical Engineers Series A, Nov. 25, 2012, vol. 78, No. 795, pp. 1495 to 1505.

* cited by examiner

FIG. 5
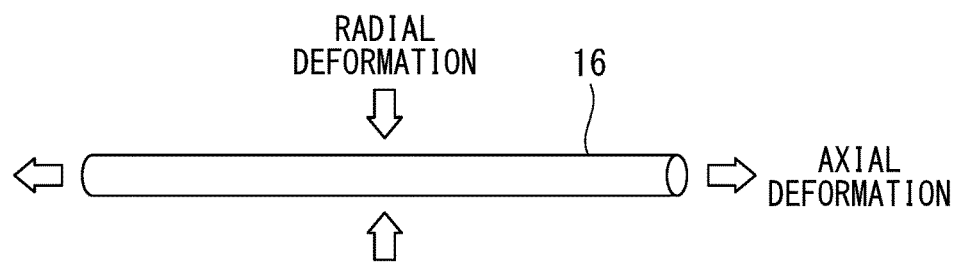
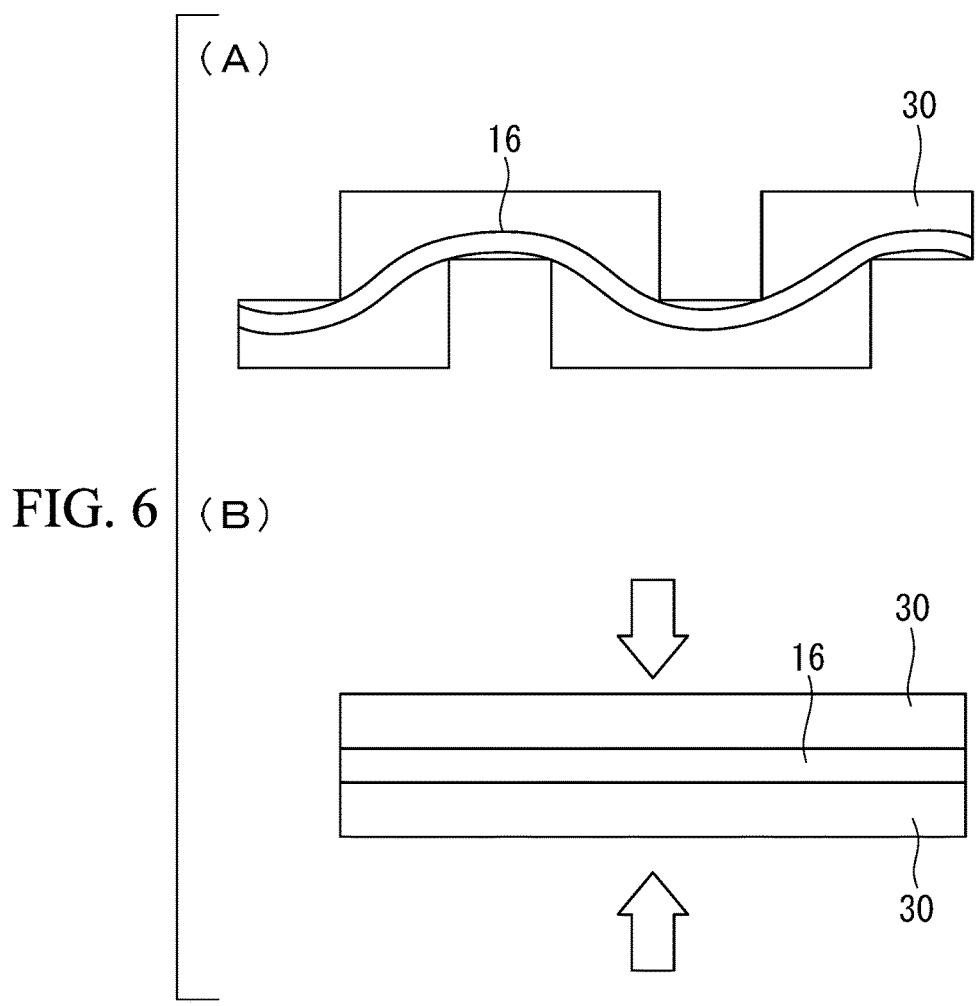
FIG. 6

BONDED STRUCTURE, METHOD FOR MANUFACTURING THE SAME, AND BONDING STATE DETECTION METHOD

TECHNICAL FIELD

The present invention relates to a bonded structure, a method for manufacturing the same, and a bonding state detection method.

BACKGROUND ART

Conventionally, carbon fiber composite materials have been used in structures such as aircraft structures where weight reduction is required.

An example of a method used for monitoring the resin curing of carbon fiber composite materials is a method using an optical fiber provided with an internal grating sensor, such as the method disclosed in Patent Literature (PTL) 1.

Members of carbon fiber composite materials are generally joined together using fasteners such as rivets or bolts.

When joining members together, using an adhesive is optimal in terms of factors such as weight reduction and operational efficiency, but evaluation of the bond quality is necessary. Evaluation of the bond quality is performed by bonding the members together with an adhesive, and then conducting an ultrasonic flaw detection inspection or the like.

CITATION LIST

Patent Literature

{PTL 1} Japanese Translation of PCT International Application, Publication No. 2000-501176

SUMMARY OF INVENTION

Technical Problem

However, in an ultrasonic flaw detection inspection, although defects such as voids in the adhesive layer or peeling of the members can be detected, the bonding strength cannot be evaluated. This is because the bonding strength depends on factors such as the pressure applied to the members during bonding, and pressure cannot be examined in an ultrasonic flaw detection inspection. Moreover, ultrasonic flaw detection inspections require considerable time and effort, and also require that the inspector is appropriately qualified.

When carbon fiber composite materials are used as members, bonding of the members is conducted, for example, during autoclave molding. During autoclave molding, although the autoclave pressure and the bag pressure are measured, the pressure of the bond itself is not measured.

As a result of these circumstances, when members are joined together by bonding, the resulting structures have significant safety tolerances, and therefore in those locations where safety is particularly important, the members tend to be joined by fasteners rather than bonded using an adhesive.

The present invention has been developed in light of these circumstances, and has an object of providing a bonded structure, a method for manufacturing the same, and a bonding state detection method which are capable of determining whether or not members are bonded together appropriately.

Solution to Problem

In order to achieve the above object, the bonded structure, the method for manufacturing the same, and the bonding state detection method according to the present invention employ the following aspects.

A bonded structure according to a first aspect of the present invention includes a first member, a second member, an adhesive that bonds the first member and the second member together, and a distributed optical fiber that is sandwiched between the first member and the second member, wherein the cross-sectional shape of the distributed optical fiber deforms in accordance with the bonding state. In this first aspect, the bonding state between the first member and the second member is detected on the basis of the axial deformation in the distributed optical fiber converted from the radial deformation.

According to this configuration, the first member and the second member are bonded together by applying an appropriate pressure with the adhesive disposed between the members. The distributed optical fiber sandwiched between the first member and the second member is used for detecting the bonding state between the first member and the second member.

Optical fibers include multipoint optical fibers and distributed optical fibers.

In multipoint optical fibers, a diffraction grating provided in a non-continuous manner in the optical fiber functions as a sensor. Accordingly, when a multipoint optical fiber is used as a pressure sensor, the bonding state can only be detected at positions where the grating is provided, namely only at non-continuous locations along the axial direction of the multipoint optical fiber, meaning there are locations where detection of the bonding state is impossible.

On the other hand, in the case of distributed optical fibers, the entire fiber in the axial direction functions as a sensor. Further, changes in the optical spectrum in the distributed optical fiber are relatively insensitive to radial deformation in the distributed optical fiber, but very sensitive to axial deformation. Accordingly, in this configuration, by converting radial deformation in the distributed optical fiber into axial deformation, the pressure applied to the distributed optical fiber is detected on the basis of this axial deformation. As a result, the distributed optical fiber can be used to continuously detect the bonding state between the first member and the second member.

As described above, in this configuration, by converting radial deformation in the distributed optical fiber into axial deformation, the bonding state can be detected continuously along the axial direction of the distributed optical fiber, meaning a determination can be made as to whether or not the members are bonded together appropriately.

In the first aspect described above, the distributed optical fiber has a property of contracting or expanding when the first member and the second member reach a bonded state compared with the case where the first member and the second member are in an unbonded state.

According to this configuration, the distributed optical fiber contracts or expands when the first member and the second member reach a bonded state. This contraction or expansion of the distributed optical fiber means radial deformation of the distributed optical fiber has been converted to axial deformation.

Accordingly, this configuration can easily convert radial deformation in the distributed optical fiber to axial deformation.

In the first aspect described above, when the first member and the second member are in an unbonded state, the distributed optical fiber may be arranged in a wave-like shape relative to the direction of the first member and the second member.

According to this configuration, by arranging the distributed optical fiber in a wave-like shape in an unbonded state, when the first member and the second member reach a bonded state and pressure is applied in the radial direction of the distributed optical fiber, the distributed optical fiber contracts linearly. Accordingly, in this configuration, radial deformation in the distributed optical fiber can be easily converted to axial deformation.

In the first aspect described above, the distributed optical fiber may be sandwiched between the first member and the second member via a wave-like member having a wave-like surface.

According to this configuration, the distributed optical fiber can be easily arranged in a wave-like shape.

In the first aspect described above, the surface of the adhesive that contacts the distributed optical fiber may have a wave-like shape.

According to this configuration, the distributed optical fiber can be easily arranged in a wave-like shape.

In the first aspect described above, at least one of the first member and the second member may have a wave-like surface that contacts the distributed optical fiber.

According to this configuration, the distributed optical fiber can be easily arranged in a wave-like shape.

In the first aspect described above, the cladding that coats the core of the distributed optical fiber may be formed with repeating large diameter sections and small diameter sections.

According to this configuration, when pressure is applied in the radial direction of the distributed optical fiber, the large diameter sections contract, whereas the small diameter sections expand. As a result, the core of the distributed optical fiber expands in the axial direction.

Accordingly, this configuration can easily convert radial deformation in the distributed optical fiber to axial deformation.

In the first aspect described above, the distributed optical fiber may be sandwiched between the first member and the second member in a state embedded in a flexible member. The flexible member has an optical fiber embedment portion in which the distributed optical fiber is embedded, and a plurality of feet protruding from the optical fiber embedment portion, with the plurality of feet arranged with spaces therebetween.

According to this configuration, by embedding the distributed optical fiber in a flexible member, and then disposing the flexible member between the first member and the second member, when the first member and the second member reach a bonded state and pressure is applied in the radial direction of the distributed optical fiber, the distributed optical fiber expands. As a result, this configuration can easily convert radial deformation in the distributed optical fiber to axial deformation.

A method for manufacturing a bonded structure according to a second aspect of the present invention includes a step of applying an adhesive to at least one of a first member and a second member, and a step of sandwiching a distributed optical fiber between the first member and the second member to which the adhesive has been applied, and applying pressure, thereby deforming the cross-sectional shape of the distributed optical fiber and bonding the first member and the second member together.

In the second aspect described above, the radial deformation in the distributed optical fiber that occurs as a result of the pressure application is converted to axial deformation, and the bonding state between the first member and the second member is detected on the basis of this axial deformation.

In the second aspect described above, the distributed optical fiber is formed from a material that has a property of contracting or expanding when the first member and the second member reach a bonded state compared with the case where the first member and the second member are in an unbonded state.

In the second aspect described above, when the first member and the second member are in an unbonded state, the distributed optical fiber may be arranged in a wave-like shape relative to the direction of the first member and the second member.

In the second aspect described above, the distributed optical fiber may be sandwiched between the first member and the second member via a wave-like member having a wave-like surface.

In the second aspect described above, the surface of the adhesive that contacts the distributed optical fiber may have a wave-like shape.

In the second aspect described above, at least one of the first member and the second member may be formed with a wave-like surface that contacts the distributed optical fiber.

In the second aspect described above, the distributed optical fiber may be sandwiched between the first member and the second member via a flexible member having an optical fiber embedment portion in which the distributed optical fiber is embedded and a plurality of feet protruding from the optical fiber embedment portion and arranged with spaces therebetween.

A bonding state detection method according to a third aspect of the present invention includes a first step of bonding a first member and a second member with an adhesive while sandwiching a distributed optical fiber between the members, and a second step of detecting the bonding state between the first member and the second member on the basis of the axial deformation in the distributed optical fiber converted from the radial deformation.

In the third aspect described above, the distributed optical fiber may be arranged on the first member, a release film, the aforementioned adhesive and the second member then stacked thereon and pressure applied, and the appropriateness of the pressure then detected by the distributed optical fiber.

Advantageous Effects of Invention

The present invention has the excellent effect of enabling a determination to be made as to whether or not members are bonded together appropriately.

BRIEF DESCRIPTION OF DRAWINGS

FIG. 5 A schematic view designating radial deformation and axial deformation of a distributed optical fiber according to the first embodiment of the present invention.

FIG. 6 Schematic views illustrating the arrangement of a distributed optical fiber according to the first embodiment of the present invention, wherein (A) illustrates an unbonded state, and (B) illustrates a bonded state.

DESCRIPTION OF EMBODIMENTS

Embodiments of the bonded structure and the bonding state detection method of the present invention are described below with reference to the drawings.

{First Embodiment}

A first embodiment of the present invention is described below.

Figure 1:
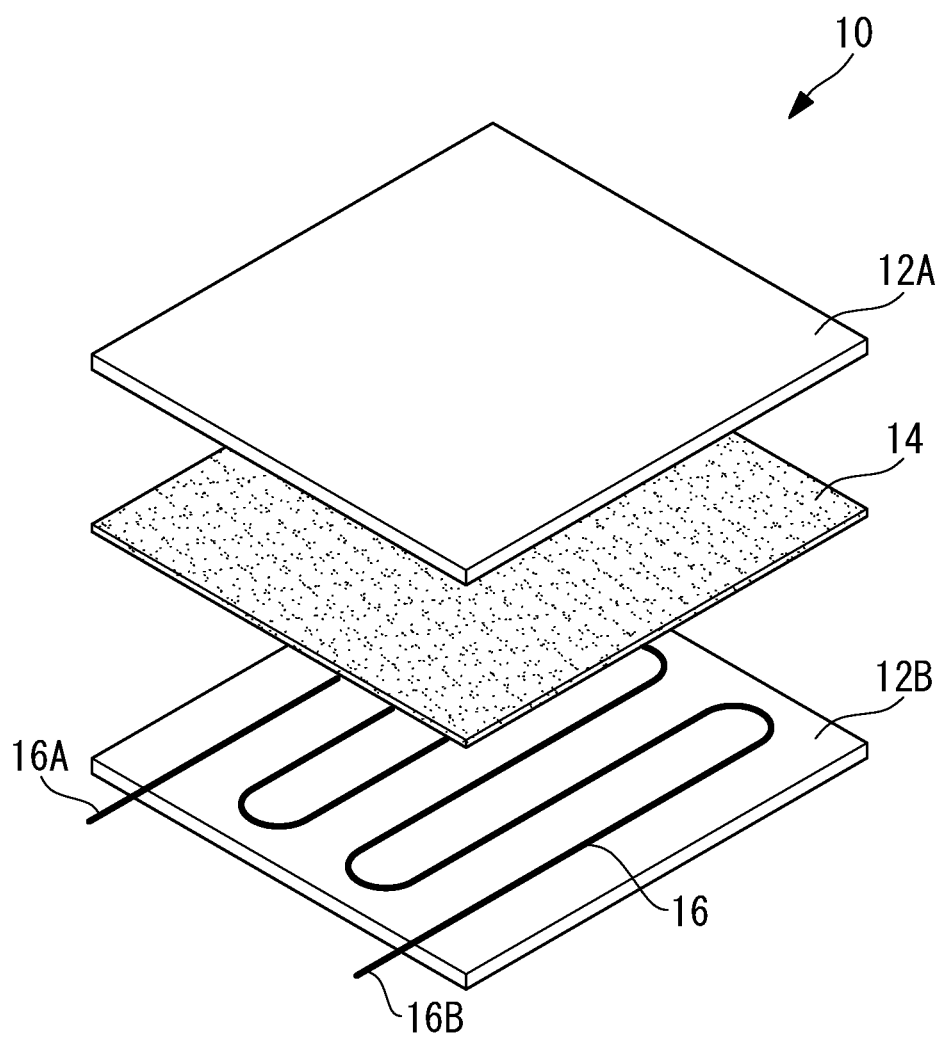
FIG. 1 An exploded perspective view illustrating a bonded structure according to a first embodiment of the present invention.

FIG. 1 is an exploded perspective view illustrating a bonded structure 10 according to the first embodiment. In the first embodiment, laminated sheets of a carbon fiber composite material are used as examples of the members to be bonded. By combining a plurality of structures, the bonded structure 10 can be used, for example, as a structural material for aircraft, automobiles, and wind turbines and the like.

The bonded structure 10 includes a laminated sheet 12A, a laminated sheet 12B, an adhesive 14 that bonds the laminated sheet 12A and the laminated sheet 12B, and a distributed optical fiber 16 that is sandwiched between the laminated sheet 12A and the laminated sheet 12B. The distributed optical fiber 16 is used as a pressure sensor for detecting the bonding state between the laminated sheet 12A and the laminated sheet 12B based on the axial deformation of the optical fiber. Details concerning the axial deformation are described below. The distributed optical fiber 16 is, for example, a single-mode fiber having a cladding diameter of 125 μm and having a circular cross-sectional shape.

The distributed optical fiber 16 has a property of contracting or expanding when the laminated sheet 12A and the laminated sheet 12B reach a bonded state compared with the case where the laminated sheet 12A and the laminated sheet 12B are in an unbonded state. The cross-sectional shape of the distributed optical fiber 16 (the transverse sectional shape perpendicular to the axial direction of the distributed optical fiber 16) when the laminated sheet 12A and the laminated sheet 12B reach a bonded state is an elliptical shape. The transverse sectional shape describes the cross-sectional shape when the distributed optical fiber 16 is cut across the length of the fiber.

The adhesive 14 is used, for example, in the form of an adhesive layer. There are no particular limitations on the type of adhesive 14 used, and for example an epoxy resin-based adhesive may be used.

Prior to bonding with the adhesive 14, at least one of the laminated sheets 12A and 12B has been cured.

The planar shapes of the laminated sheets 12A and 12B illustrated in FIG. 1 are square, but this is merely an example, and the planar shapes of the laminated sheets 12A and 12B are not limited to squares. The shapes of the laminated sheets 12A and 12B need not necessarily be planar shapes. In the example in FIG. 1, the adhesive 14 is only applied to one of the laminated sheets 12A and 12B, but this is not a limitation, and the adhesive 14 may also be applied to both of the laminated sheets 12A and 12B.

The distributed optical fiber 16 illustrated in FIG. 1 is bent a plurality of times with an end section 16A and an end section 16B both protruding from the same side of the laminated sheets 12A and 12B, but this is merely an example, and the distributed optical fiber 16 need not necessarily be sandwiched in a bent configuration, and the end section 16A and the end section 16B may protrude from different sides of the laminated sheets 12A and 12B. Input and output of light may occur at the same end section of the distributed optical fiber 16.

Figure 2:
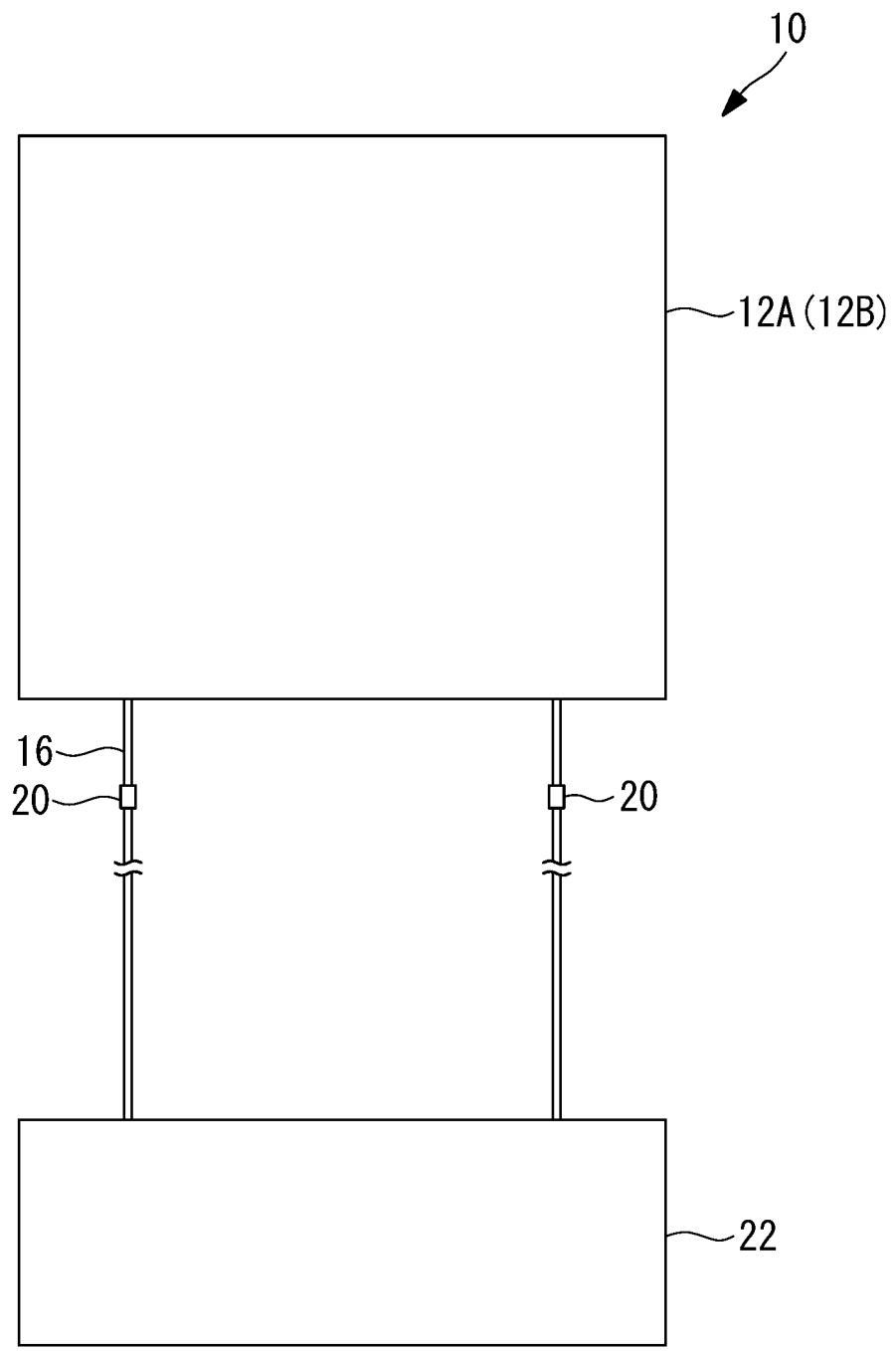
FIG. 2 A schematic plan view of a measuring diagnostic device according to the first embodiment of the present invention.

As illustrated in FIG. 2, the end sections 16A and 16B of the distributed optical fiber 16 are connected to a measuring diagnostic device 22 via connectors 20. The measuring diagnostic device 22 inputs light of a prescribed wavelength from the end section 16A (input port) of the distributed optical fiber 16, the light is reflected inside the distributed optical fiber 16, and the light exiting from the end section 16B (hereafter referred to as "reflected light") is detected and an optical spectrum is obtained.

The laminated sheets 12A and 12B are bonded together by applying pressure with the adhesive 14 sandwiched between the sheets. When pressure is applied to the laminated sheets 12A and 12B, pressure is also applied to the distributed optical fiber 16. In the following description, the application of pressure to the laminated sheets 12A and 12B is also referred to as "compression".

Birefringence in an optical fiber 15 is described below with reference to FIGS. 3 and 4.

Figure 3:
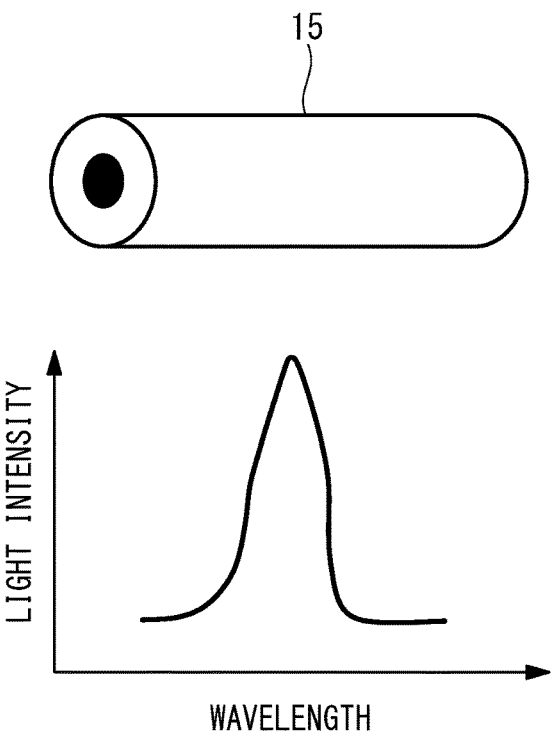
FIG. 3 A diagram illustrating the optical spectrum when no pressure is applied to an optical fiber according to the first embodiment of the present invention.
Figure 4:
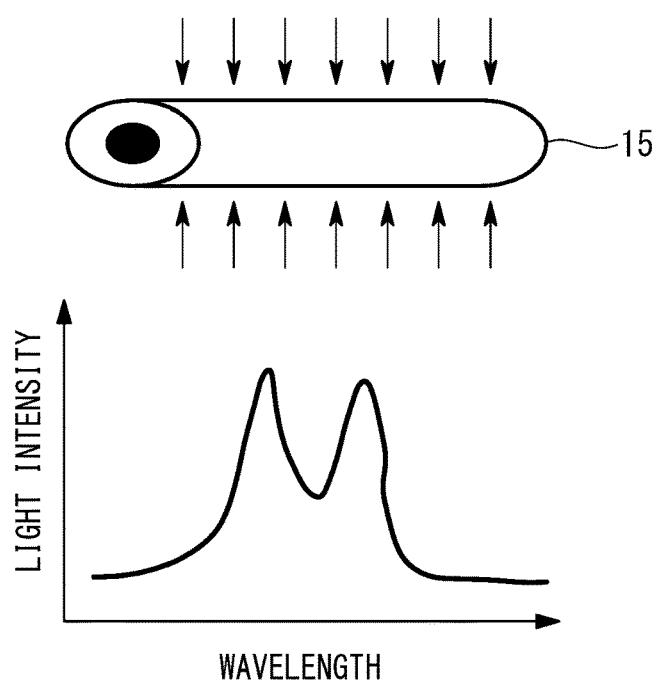
FIG. 4 A diagram illustrating the optical spectrum when pressure is applied to an optical fiber according to the first embodiment of the present invention.

In a state where no pressure is applied to the optical fiber 15, the optical spectrum has a single peak, as illustrated in FIG. 3. In contrast, when pressure is applied to the optical fiber 15 from only a prescribed direction (the vertical direction in FIGS. 3 and 4), then as illustrated in FIG. 4, the cross-sectional shape of the optical fiber 15, which was circular, deforms and changes, for example to an elliptical shape (a flattened circle or oval shape). As a result, the optical spectrum changes to a shape having multiple (for example two) peaks. This is birefringence of the optical fiber 15. When the laminated sheets 12A and 12B are bonded together by application of pressure, the optical fiber 15 sandwiched between the laminated sheets 12A and 12B deforms mainly in the radial direction.

Examples of the optical fiber 15 include multipoint optical fibers and the distributed optical fiber 16 used in the first embodiment.

In multipoint optical fibers, a diffraction grating provided in a non-continuous manner in the core functions as a sensor. In multipoint optical fibers, the optical spectrum is sensitive to radial deformation in the multipoint optical fiber. In other words, when pressure is applied, the optical spectrum output from the multipoint optical fiber changes in the manner described using FIGS. 3 and 4.

However, if a multipoint optical fiber is used as a pressure sensor, then pressure detection can only be conducted at locations where the grating is provided. In other words, the bonding state can only be detected at non-continuous locations along the axial direction of the multipoint optical fiber. As a result, locations where the grating is not provided are excluded from detection of the bonding state.

On the other hand, the distributed optical fiber 16 used in the first embodiment functions as a sensor along the entire length of the fiber in the axial direction. Changes in the optical spectrum in the distributed optical fiber 16 are relatively insensitive to radial deformation of the distributed optical fiber, but very sensitive to axial deformation.

Accordingly, in order to detect the bonding state between the laminated sheet 12A and the laminated sheet 12B using the distributed optical fiber 16 that is sensitive to axial deformation, the bonded structure 10 according to the first embodiment converts radial deformation in the distributed optical fiber 16 into axial deformation, as illustrated in FIG. 5.

When the distributed optical fiber 16 deforms in the axial direction, namely contracts or expands, the peak position of the reflected light differs from the position prior to contraction or expansion. Accordingly, by measuring the displacement in the peak position of the reflected light before and after the contraction or expansion, the amount of deformation (amount of strain) in the axial direction of the distributed optical fiber 16 can be detected. As described above, the amount of deformation (amount of strain) in the axial direction indicates the bonding state between the laminated sheets 12A and 12B.

Accordingly, in the bonded structure 10 used in the first embodiment, axial deformation in the distributed optical fiber 16 can be used to detect the bonding state between the laminated sheet 12A and the laminated sheet 12B continuously along the axial direction of the distributed optical fiber 16.

In the first embodiment, in which the members to be bonded are the laminated sheets 12A and 12B of a carbon composite material, when the pressure device (in the first embodiment, an autoclave is one possible example) is used to bond the laminated sheets 12A and 12B, the bonding state is detected by the distributed optical fiber 16. Accordingly, in the first embodiment, when the laminated sheets 12A and 12B of a carbon composite material are bonded together as members, a determination can be made as to whether or not the members have been bonded together appropriately.

Next is a description of specific methods for converting radial deformation in the distributed optical fiber 16 into axial deformation.

The distributed optical fiber 16 according to the first embodiment is arranged so that when the laminated sheet 12A and the laminated sheet 12B reach a bonded state, the optical fiber contracts or expands compared with the case where the laminated sheet 12A and the laminated sheet 12B are in an unbonded state.

When the laminated sheet 12A and the laminated sheet 12B reach a bonded state, the contraction or expansion of the distributed optical fiber 16 accompanying the application of pressure in the radial direction of the distributed optical fiber 16 means that radial deformation in the distributed optical fiber 16 has been converted to axial deformation.

FIG. 6 (FIG. 6(A) and FIG. 6(B)) are schematic views illustrating an example of the arrangement of the distributed optical fiber 16 according to the first embodiment of the present invention. In FIG. 6 (FIG. 6(A) and FIG. 6(B)), the distributed optical fiber 16 is embedded in a sensitivity improvement element described below.

FIG. 6(A) illustrates the case where the laminated sheet 12A (not shown in the drawing) and the laminated sheet 12B (not shown in the drawing) are in an unbonded state (an uncompressed state).

When the laminated sheet 12A and the laminated sheet 12B are in an unbonded state, the distributed optical fiber 16 is arranged in a wave-like shape relative to the direction of the laminated sheet 12A and the laminated sheet 12B. In other words, the distributed optical fiber 16 is arranged so that the direction of the curves (the inflection points) of the optical fiber is along the lamination direction of the laminated sheet 12A and the laminated sheet 12B.

FIG. 6(B) illustrates the case where the laminated sheet 12A and the laminated sheet 12B are in a bonded state.

As illustrated in FIG. 6(B), when pressure is applied in the radial direction of the distributed optical fiber 16 in order to bond the laminated sheet 12A and the laminated sheet 12B together, a force is applied in substantially a perpendicular direction to the compression direction, and linear deformation of the wave-like arranged distributed optical fiber 16 causes contraction in the axial direction. As a result, the radial deformation in the distributed optical fiber 16 is easily converted to axial deformation.

Figure 7:
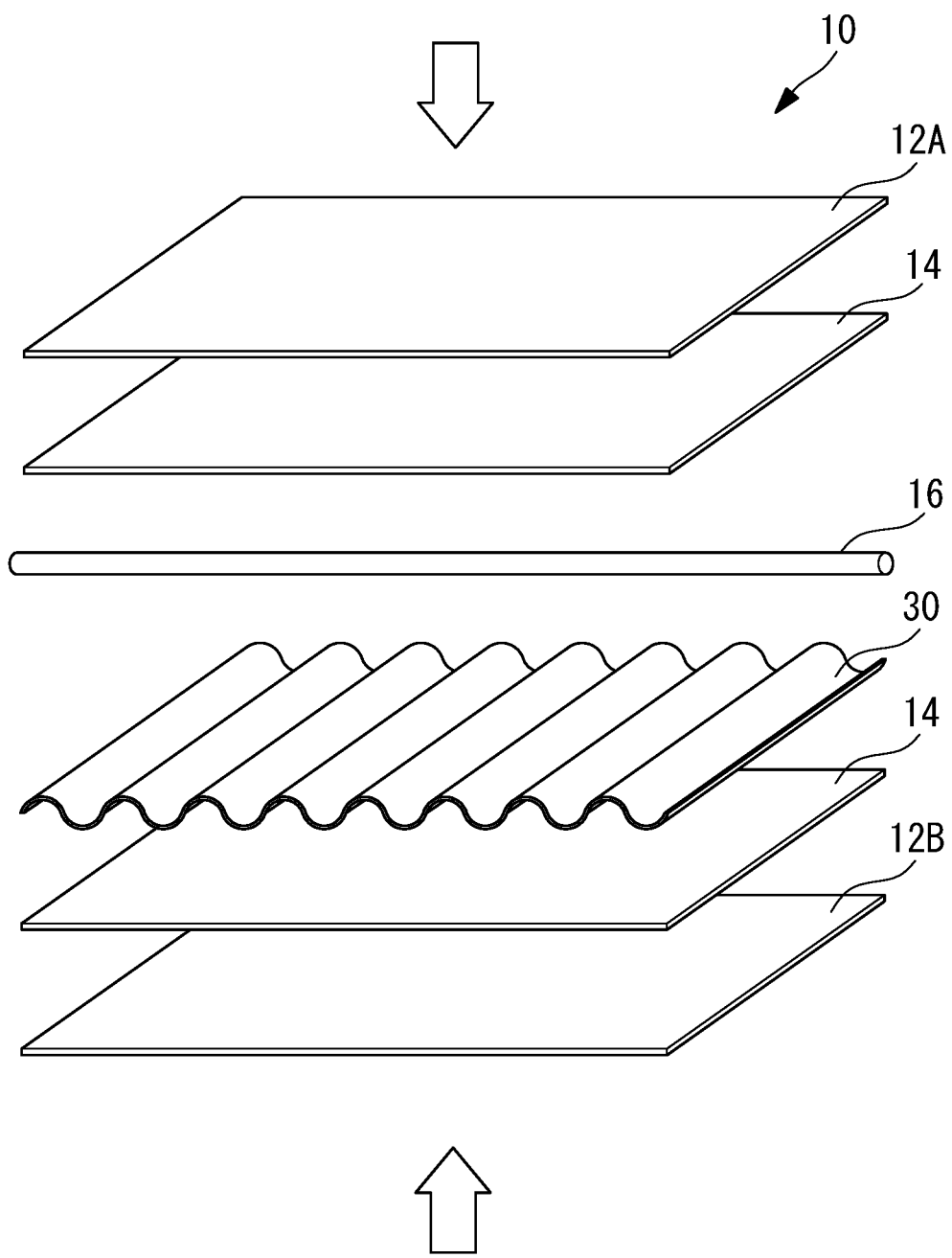
FIG. 7 A schematic view illustrating the arrangement of a distributed optical fiber according to the first embodiment of the present invention.

FIG. 7 is a schematic view illustrating the arrangement of the distributed optical fiber 16 according to the first embodiment. As illustrated in FIG. 7, the distributed optical fiber 16 according to the first embodiment is sandwiched between the laminated sheet 12A and the laminated sheet 12B via a sensitivity improvement element 30. The sensitivity improvement element 30 is a wave-like member having a wave-shaped surface.

This wave-like shape could also be described as a shape having continuous undulations. The wave-like shape may have arc shaped undulations as illustrated in the example of FIG. 7, or polygonal undulations such as triangular or square shapes.

The sensitivity improvement element 30 may, for example, be a cured adhesive of an adhesive such as a chemical-curing, thermosetting or thermoplastic adhesive.

A chemical-curing adhesive is an adhesive in which, for example, the curing reaction is initiated by mixing two liquids composed of a main agent and a curing agent respectively. An example of a chemical-curing adhesive is EA9394 manufactured by Henkel Corporation.

a thermosetting adhesive is an adhesive that undergoes a curing reaction by application of external heat to the adhesive. An example of a thermosetting adhesive is FM300-2 manufactured by Cytec Solvay Group.

A thermoplastic adhesive is an adhesive in which a polymerization reaction is initiated by applying heat to the adhesive, and the curing reaction then proceeds upon heat dissipation. An example of a thermoplastic adhesive is PPS resin (Poly Phenylene Sulfide resin).

A shim of an uncured prepreg or the like used for regulating the space between the bonded portions may be used as the sensitivity improvement element 30.

In the first embodiment, an element prepared by curing the aforementioned FM300-2 manufactured by Cytec Solvay Group was used as one example of the sensitivity improvement element 30. In one example of the first embodiment, FM300-2 manufactured by Cytec Solvay Group was also used as the adhesive 14.

In this manner, by forming the sensitivity improvement element 30 by curing the same adhesive as that used for the adhesive 14, the sensitivity improvement element 30 and the adhesive 14 can be integrated (assimilated) during the bonding process for the bonded structure 10, meaning the sensitivity improvement element 30 does not become an impurity within the bonded structure 10. As a result, the strength does not deteriorate near the locations where the sensitivity improvement element 30 has been inserted.

Which of a chemical-curing adhesive, a thermosetting adhesive and a thermoplastic adhesive is selected for the sensitivity improvement element 30 can be determined as appropriate based on factors such as the shape of the sensitivity improvement element 30 and the type of adhesive 14 used.

Figure 8:
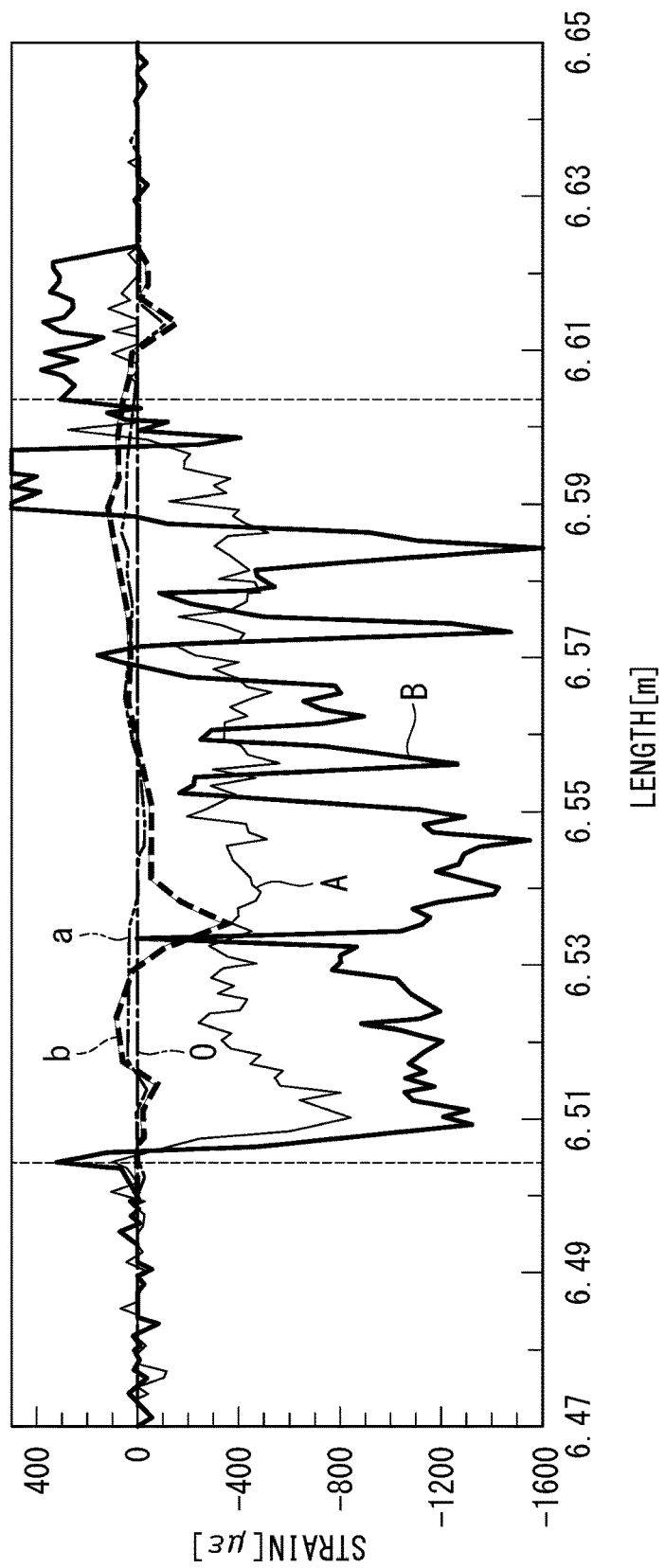
FIG. 8 A graph illustrating the test results for a bonded structure using a sensitivity improvement element according to the first embodiment of the present invention.

FIG. 8 illustrates the test results (dashed lines a and b) for a bonded structure 10 according to the first embodiment that does not use the sensitivity improvement element 30, and the test results (solid lines A and B) for a bonded structure 10 using the sensitivity improvement element 30. The test piece was, for example, a bonded structure 10 in which the distributed optical fiber 16 was sandwiched between the sensitivity improvement element 30 and the laminated sheets 12A and 12B composed of aluminum sheets, with pressure applied to this bonded structure 10 from the vertical direction.

The "Length (m)" shown along the horizontal axis of FIG. 8 represents the length of the distributed optical fiber 16, and indicates the position of pressure detection. The "Strain ($\mu\varepsilon$)" shown along the vertical axis of FIG. 8 is a value indicating the strain in the axial direction of the distributed optical fiber 16, wherein a positive value indicates an expansion and a negative value indicates a contraction.

In the test, the portion where pressure was applied to the bonded structure 10 (hereafter referred to as the "compressed portion") is from about 6.5 m to 6.6 m. The pressure applied to the bonded structure 10 in the test was 0.1 MPa (dashed line a and solid line A) or 0.4 MPa (dashed line b and solid line B).

In FIG. 8, the dot and dash line O represents the case where the pressure is 0 MPa, namely the case where no compression was applied, and represents no axial strain as indicated by Strain=0.

The dashed lines a and b indicating the test results for the bonded structure 10 not using the sensitivity improvement element 30 displayed slight fluctuations in the axial strain in the compressed portion, but the changes did not exhibit good sensitivity to the pressure.

On the other hand, the solid lines A and B representing the test results for the bonded structure 10 using the sensitivity improvement element 30 show large changes in the negative value of the axial strain in the compressed portion. The changes in the solid line B (0.4 MPa) that indicates the test conducted at higher pressure were larger than the changes in the solid line A (0.1 MPa).

In the solid lines A and B, based on the fact that a negative change in the axial strain occurs continuously in the compressed portion, it is evident that the bonded structure 10 using the sensitivity improvement element 30 is continuously detecting the bonding state.

By preparing in advance information (for example, tabulated information) indicating the relationship between the size of the axial strain and the pressure, and then referencing the tabulated information against actually measured axial strain values, the pressure applied to the bonded structure 10 can be determined from the measured axial strain.

As described above, the bonded structure 10 according to the first embodiment includes the laminated sheet 12A, the laminated sheet 12B, the adhesive 14 that bonds the laminated sheet 12A and the laminated sheet 12B together, and the distributed optical fiber 16 sandwiched between the laminated sheet 12A and the laminated sheet 12B. The bonding state between the laminated sheet 12A and the laminated sheet 12B is detected on the basis of the axial deformation in the distributed optical fiber 16 converted from the radial deformation.

In this manner, in the bonded structure 10 according to the first embodiment, the bonding state can be detected continuously along the axial direction of the distributed optical fiber 16 by converting the radial deformation in the distributed optical fiber 16 to axial deformation, and therefore a determination can be made as to whether or not the members have been appropriately bonded together.

More specifically, in the case where pressure is applied during the bonding step for the bonded structure 10, the quality following bonding has conventionally been confirmed by detecting the pressure applied to the entire bonded structure 10, but because the distributed optical fiber 16 enables the pressure to be detected at the actual bonding location, the adequacy of the bonding step can be evaluated more precisely.

{Second Embodiment}

A second embodiment of the present invention is described below.

Figure 9:
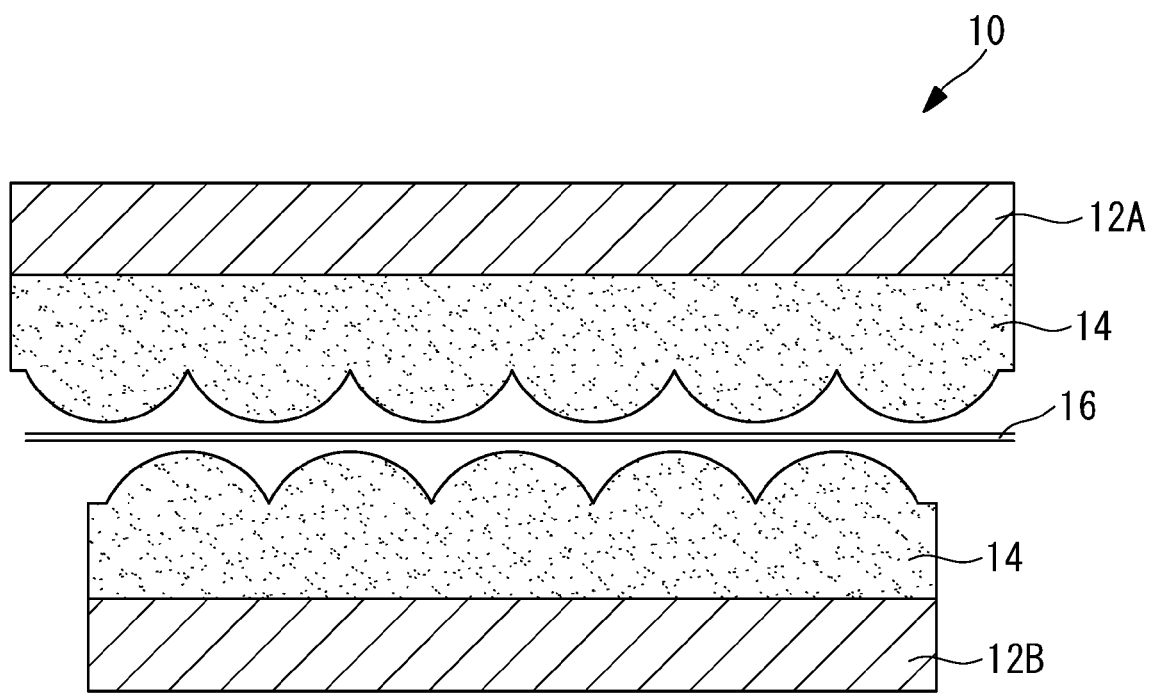
FIG. 9 A longitudinal sectional view illustrating the configuration of a bonded structure according to a second embodiment of the present invention.
Figure 10:
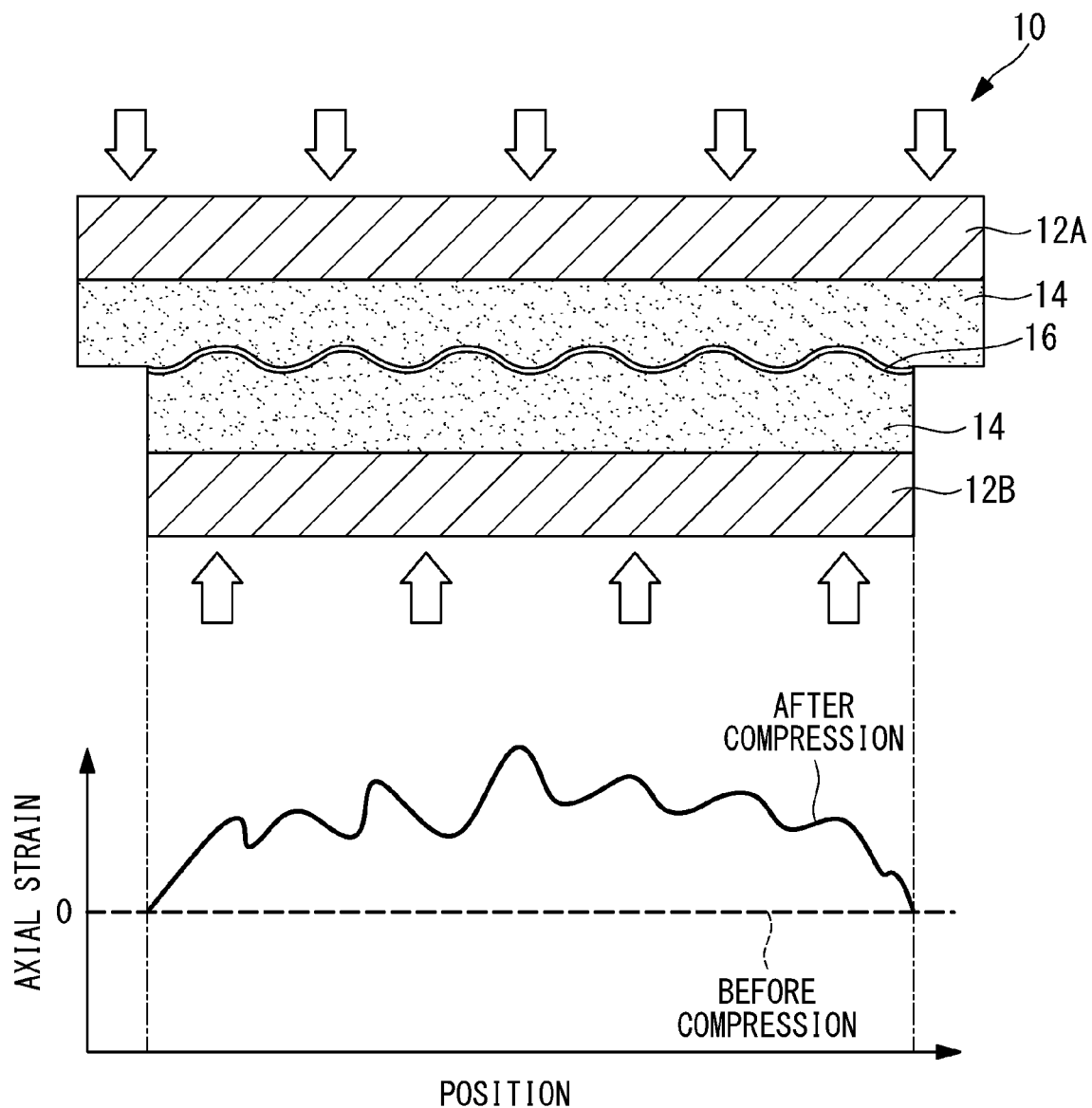
FIG. 10 A schematic view illustrating the positional change in axial strain before and after compression of a bonded structure according to the second embodiment of the present invention.

FIG. 9 is a longitudinal sectional view illustrating the configuration of a bonded structure 10 according to the second embodiment prior to the application of pressure. Structural items in FIG. 9 that are the same as items in FIG. 7 are labeled using the same signs as FIG. 7, and description of these items is omitted. FIG. 10 is a schematic view illustrating the positional change in axial strain before and after compression of the bonded structure 10 according to the second embodiment. In FIG. 10, the case where axial strain occurs as contraction of the distributed optical fiber 16 is represented by a change in the positive direction.

As illustrated in FIG. 9, in the bonded structure 10 according to the second embodiment, the adhesive 14 (adhesive layer) is applied so that the surface of the adhesive that contacts the distributed optical fiber 16 has a wave-like shape. As a result, the bonded structure 10 according to the second embodiment enables the distributed optical fiber 16 to be easily arranged in a wave-like shape, without using the sensitivity improvement element 30 (also see FIG. 10).

As illustrated in FIG. 10, when the bonded structure 10 according to the second embodiment is compressed, the external shape of the distributed optical fiber 16 conforms to the contact surface with the adhesive layer and adopts a wave-like shape, and subsequently, the distributed optical fiber 16 contracts at that location, thereby increasing the axial strain, and meaning the bonding state in the bonded structure 10 can be detected.

{Third Embodiment}

A third embodiment of the present invention is described below.

Figure 11:
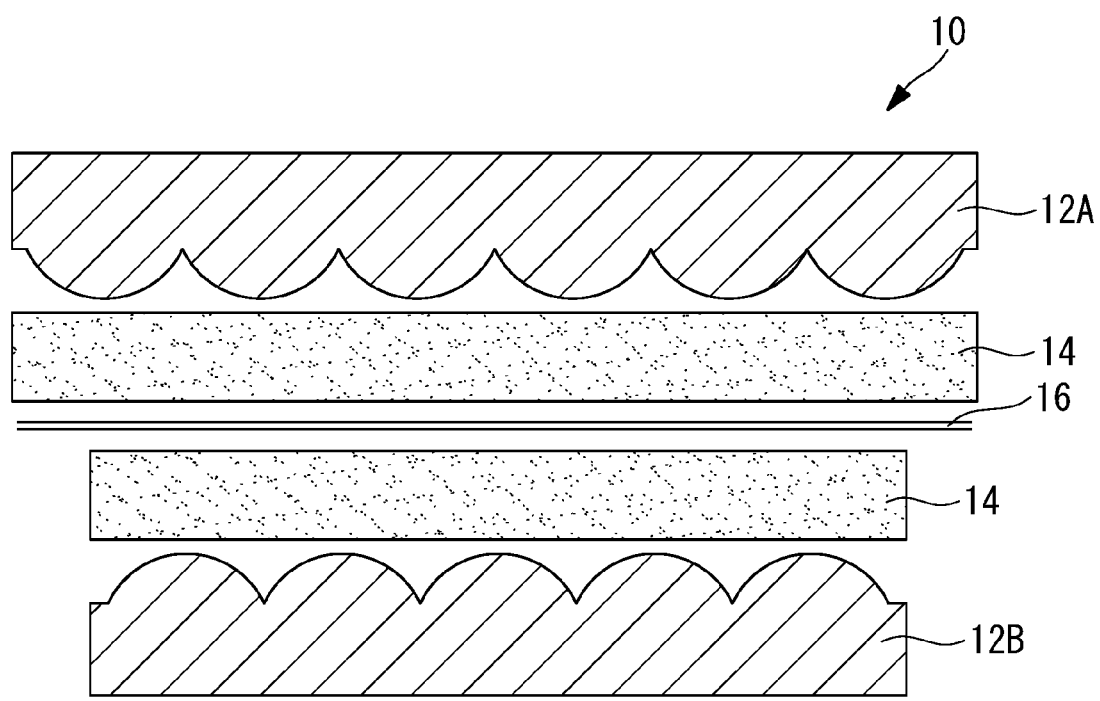
FIG. 11 A longitudinal sectional view illustrating the configuration of a bonded structure according to a third embodiment of the present invention.
Figure 12:
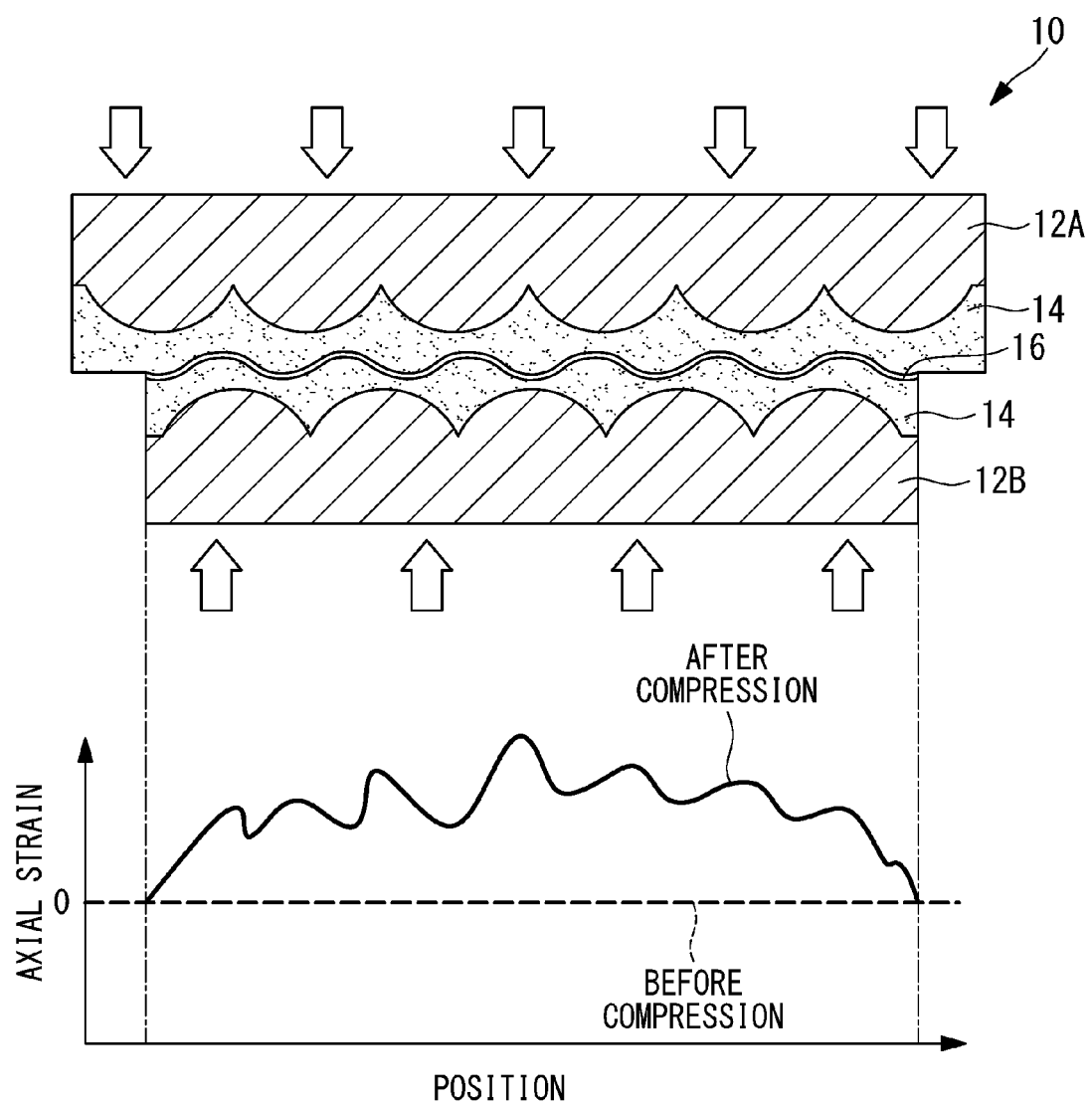
FIG. 12 A schematic view illustrating the positional change in axial strain before and after compression of a bonded structure according to the third embodiment of the present invention.

FIG. 11 is a longitudinal sectional view illustrating the configuration of a bonded structure 10 according to the third embodiment prior to the application of pressure. Structural items in FIG. 11 that are the same as items in FIG. 7 are labeled using the same signs as FIGS. 7 and 9, and description of these items is omitted. FIG. 12 is a schematic view illustrating the positional change in axial strain before and after compression of the bonded structure 10 according to the third embodiment. In FIG. 12, the case where axial strain occurs as contraction of the distributed optical fiber 16 is represented by a change in the positive direction.

As illustrated in FIG. 11, in the bonded structure 10 according to the third embodiment, the surfaces of the laminated sheet 12A and the laminated sheet 12B that contact the distributed optical fiber 16 are formed with wave-like shapes. As a result, the bonded structure 10 according to the third embodiment enables the distributed optical fiber 16 to be easily arranged in a wave-like shape, without using the sensitivity improvement element 30 (also see FIG. 12).

As illustrated in FIG. 12, when the bonded structure 10 according to the third embodiment is compressed, the external shape of the distributed optical fiber 16 conforms to the contact surface with the adhesive layer and adopts a wave-like shape, and subsequently, the distributed optical fiber 16 contracts at that location, thereby increasing the axial strain, and meaning the bonding state in the bonded structure 10 can be detected.

In the example of FIG. 11, both the laminated sheet 12A and the laminated sheet 12B are formed with wave-like surfaces, but this is not a limitation, and a configuration in which only one of the laminated sheet 12A and the laminated sheet 12B has a wave-like shape may also be used.

{Fourth Embodiment}

A fourth embodiment of the present invention is described below.

Figure 13:
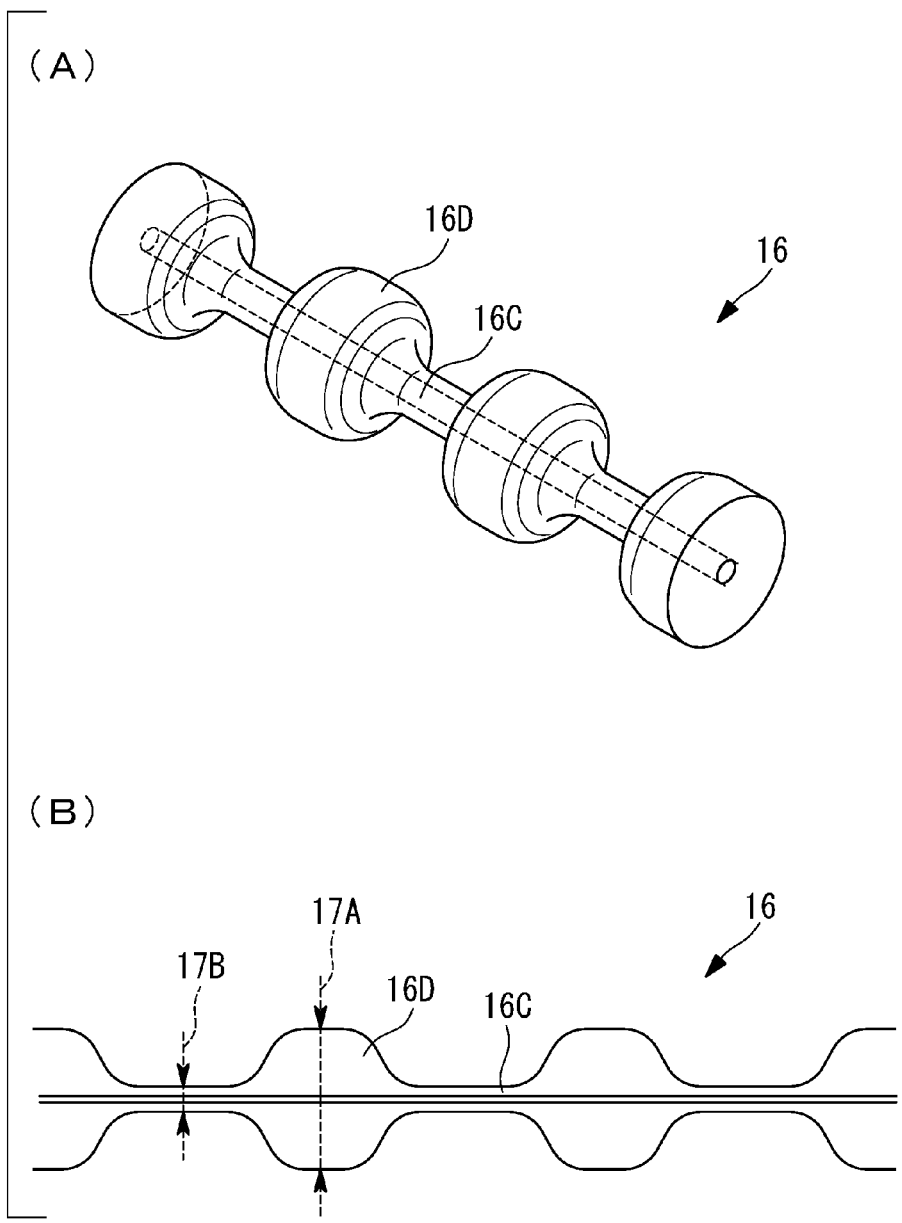
FIG. 13 Structural views of a distributed optical fiber according to a fourth embodiment of the present invention, wherein (A) is a perspective view, and (B) is a cross-sectional view.
Figure 14:
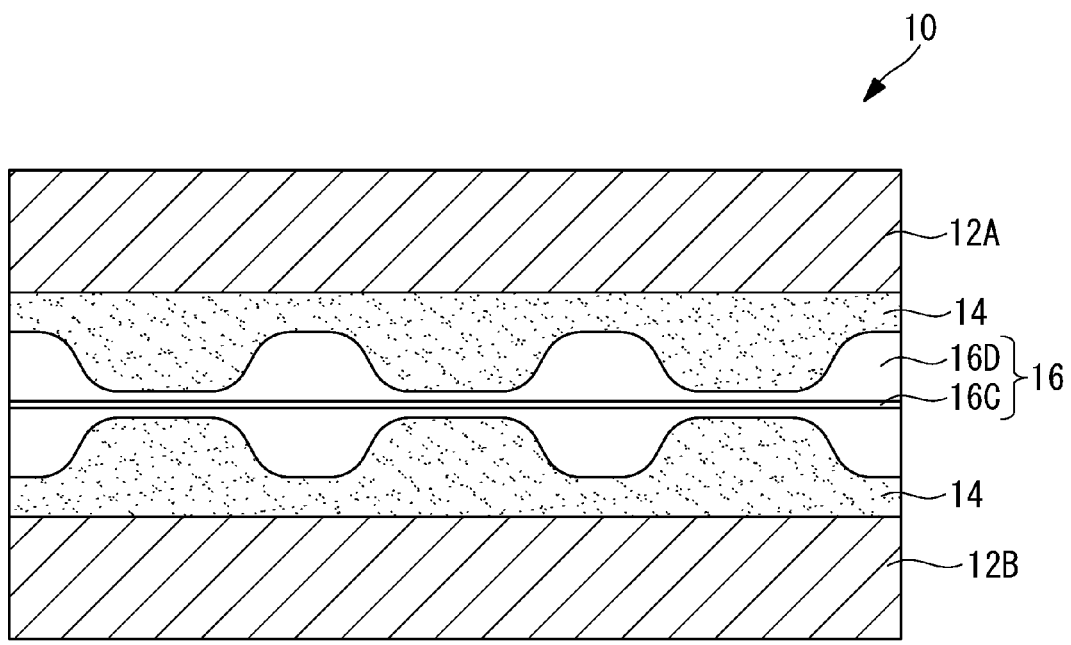
FIG. 14 A longitudinal sectional view illustrating the configuration of a bonded structure according to the fourth embodiment of the present invention.
Figure 15:
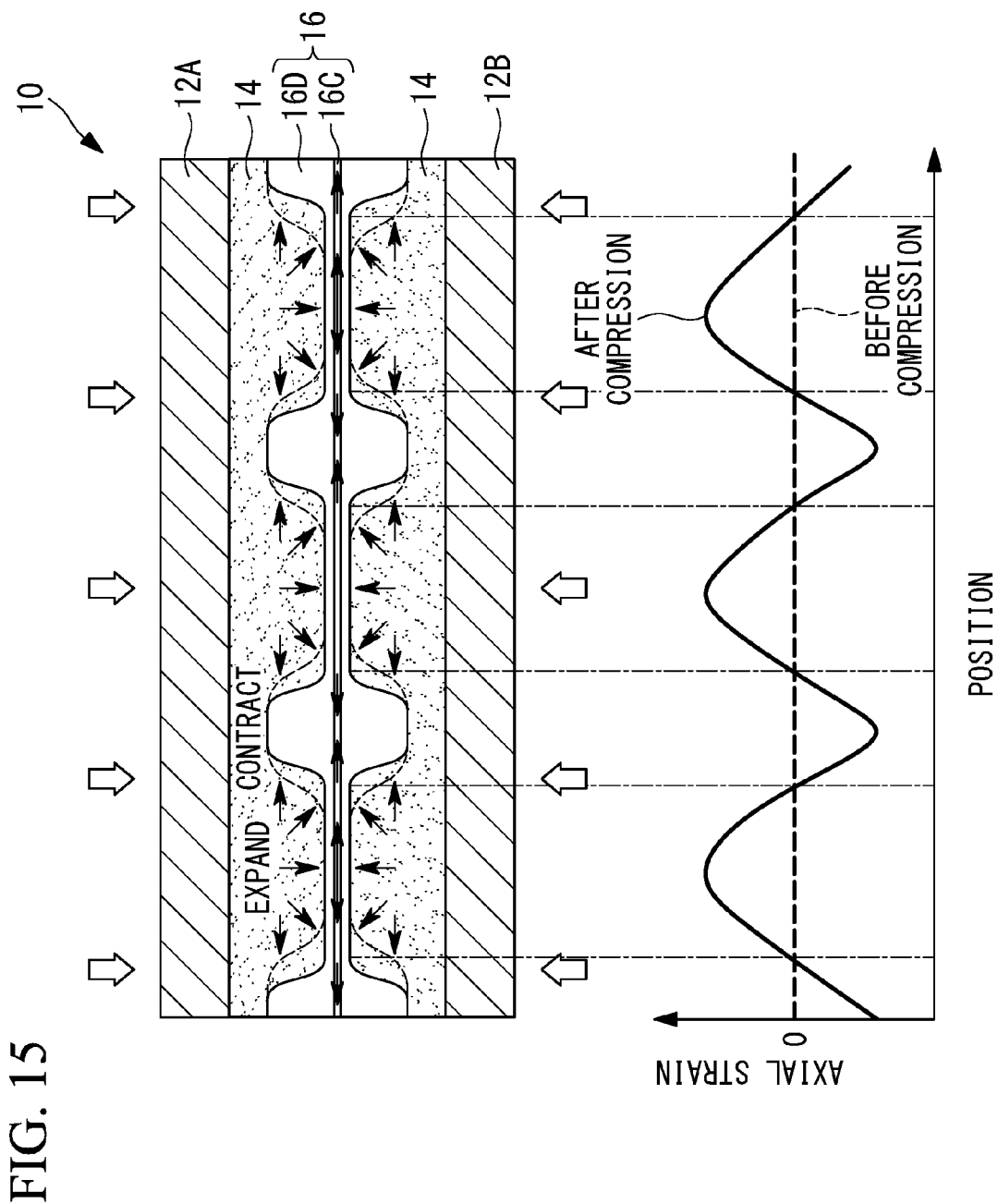
FIG. 15 A schematic view illustrating the positional change in axial strain before and after compression of a bonded structure according to the fourth embodiment of the present invention.

FIG. 13 (FIG. 13(A) and FIG. 13(B)) shows structural views of a distributed optical fiber 16 according to the fourth embodiment, wherein FIG. 13(A) is a perspective view, and FIG. 13(B) is a cross-sectional view. FIG. 14 is a longitudinal sectional view illustrating the configuration of a bonded structure 10 according to the fourth embodiment prior to the application of pressure. FIG. 15 is a schematic view illustrating the positional change in axial strain before and after compression of the bonded structure 10 according to the fourth embodiment. In FIG. 15, the case where axial strain occurs as expansion of the distributed optical fiber 16 is represented by a change in the positive direction, and the case where axial strain occurs as contraction of the distributed optical fiber 16 is represented by a change in the negative direction.

Structural items in FIG. 13 (FIG. 13(A) and FIG. 13(B)) through FIG. 15 that are the same as items in FIG. 7 are labeled using the same signs as FIG. 7, and description of these items is omitted.

As illustrated in FIG. 13 (FIG. 13(A) and FIG. 13(B)) and FIG. 14, a cladding 16D that coats a core 16C of the distributed optical fiber 16 is formed with repeating large diameter sections 17A and small diameter sections 17B. The core 16C is provided linearly along the axial center of the cladding 16D.

As illustrated in FIG. 15, when the laminated sheet 12A and the laminated sheet 12B reach a bonded state and pressure is applied in the radial direction of the distributed optical fiber 16, the large diameter sections 17A contract, while the small diameter sections 17B expand. This causes the core 16C of the distributed optical fiber 16 to expand in the axial direction.

As a result, the bonded structure 10 according to the fourth embodiment can easily convert radial deformation in the distributed optical fiber 16 to axial deformation.

As illustrated in FIG. 15, the axial strain increases in those portions where the core 16C has expanded, whereas the axial strain decreases in those portions where the core 16C has contracted, thus enabling detection of the bonding state in the bonded structure 10.

{Fifth Embodiment}

A fifth embodiment of the present invention is described below.

Figure 16:
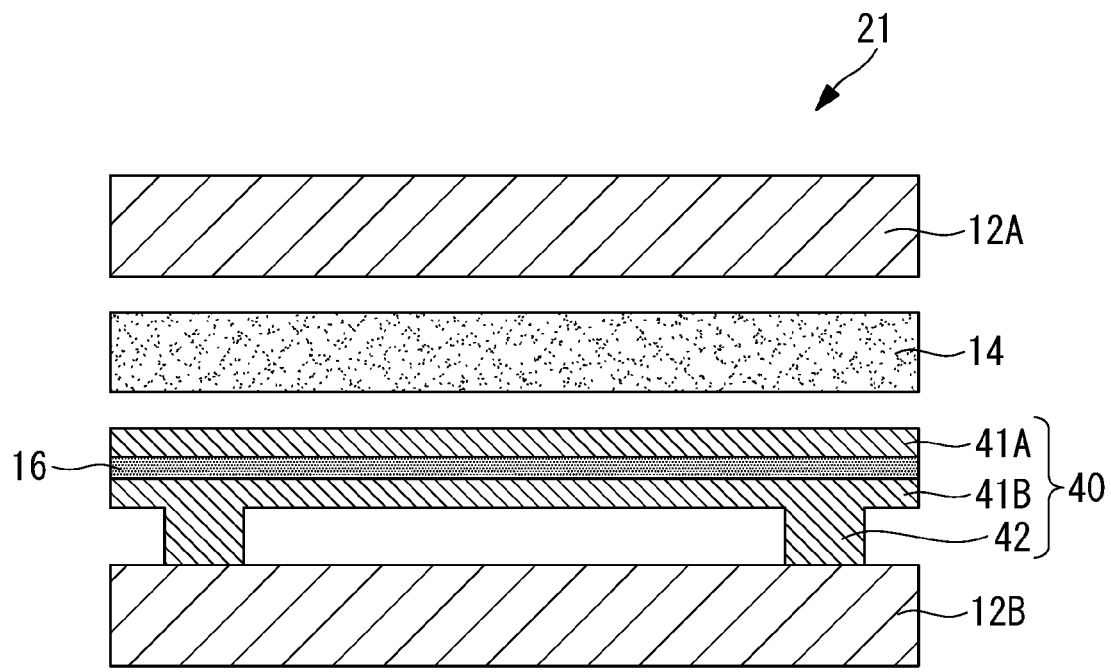
FIG. 16 A longitudinal sectional view illustrating the configuration of a bonded structure according to a fifth embodiment of the present invention.
Figure 17:
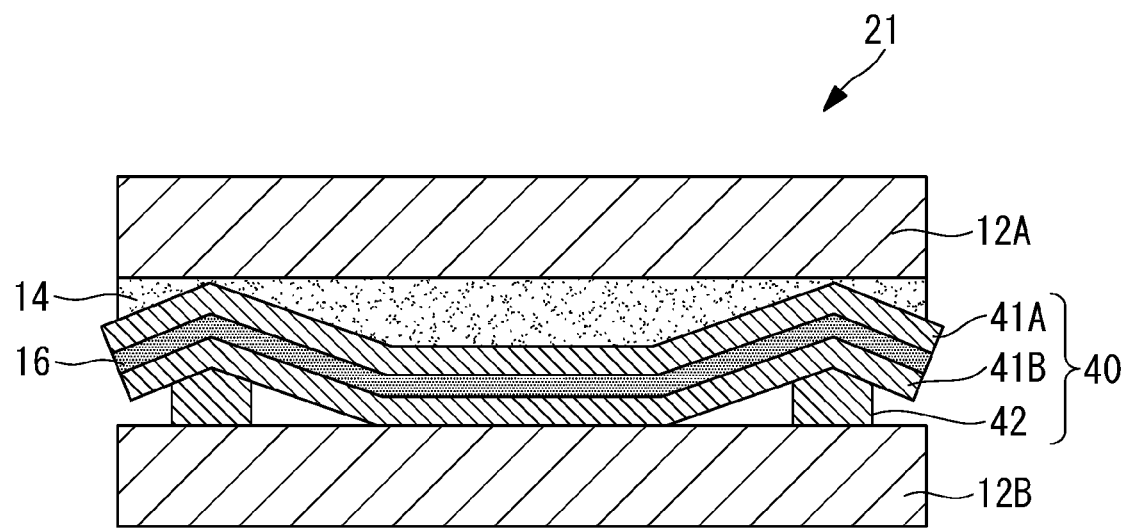
FIG. 17 A diagram illustrating the bonded structure of FIG. 16 following application of pressure in the vertical direction.
Figure 18:
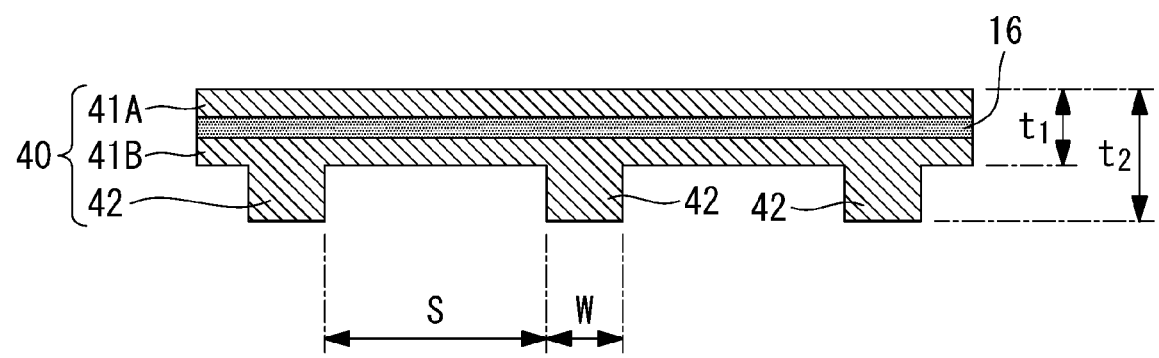
FIG. 18 A partial longitudinal sectional view illustrating the configuration of a flexible member according to the fifth embodiment of the present invention.

FIG. 16 is a longitudinal sectional view illustrating the configuration of a bonded structure 21 according to the fifth embodiment prior to the application of pressure. FIG. 17 is a diagram illustrating the bonded structure 21 of FIG. 16 following application of pressure in the vertical direction. FIG. 18 is a partial longitudinal sectional view describing a flexible member 40 according to the fifth embodiment.

Structural items in FIG. 16 to FIG. 18 that are the same as items in FIG. 7 are labeled using the same signs as FIG. 7, and description of these items is omitted.

In a similar manner to the bonded structure 10, the bonded structure 21 includes the laminated sheet 12A, the laminated sheet 12B, the adhesive 14 that bonds the laminated sheet 12A and the laminated sheet 12B, and the distributed optical fiber 16 that is sandwiched between the laminated sheet 12A and the laminated sheet 12B. The bonded structure 21 also includes the flexible member 40. The distributed optical fiber 16 is sandwiched between the laminated sheet 12A and the laminated sheet 12B via the flexible member 40.

The flexible member 40 is, for example, a cured adhesive. The adhesive may be a chemical-curing, thermosetting or thermoplastic adhesive. Which of a chemical-curing adhesive, a thermosetting adhesive and a thermoplastic adhesive is selected for the flexible member 40 can be determined as appropriate based on factors such as the shape of the flexible member 40 and the type of adhesive 14 used. By forming the flexible member 40 by curing the same adhesive as that used for the adhesive 14, the flexible member 40 and the adhesive 14 can be integrated (assimilated) during the bonding process for the bonded structure 21, meaning the flexible member 40 does not become an impurity within the bonded structure 21. As a result, the strength does not deteriorate near the locations where the flexible member 40 has been inserted.

The flexible member 40 has an optical fiber embedment portion 41 and a plurality of feet 42. In FIG. 16, the optical fiber embedment portion 41 has a sheet-like form. The distributed optical fiber 16 is embedded in the optical fiber embedment portion 41. For example, in FIG. 16, the distributed optical fiber 16 is embedded in the optical fiber embedment portion 41 by being sandwiched between an optical fiber embedment portion 41A and an optical fiber embedment portion 41B.

A thickness $t_1$ of the optical fiber embedment portion 41 with the distributed optical fiber 16 embedded therein is typically at least 10 μm but not more than 1,000 μm, and is preferably at least 50 μm but not more than 200 μm. If the thickness $t_1$ is too thin, then the optical fiber tends to become exposed through the element. If the thickness $t_1$ is too great, then there is a strong possibility that the entire element including the optical fiber may protrude from the adhesive layer. The thickness $t_1$ of the optical fiber embedment portion 41 may be set within the above range in accordance with the thickness of the adhesive (the adhesive layer) and the bonding pressure and the like.

The plurality of feet 42 are provided so as to protrude from the surface of the optical fiber embedment portion 41B. Although not indicated in FIGS. 16 to 18, the feet 42 extend across the width direction of the sheet (in the direction perpendicular to the surface of the paper). The plurality of feet 42 are arranged on the surface of the optical fiber embedment portion 41B with a prescribed spacing s between the feet. The prescribed spacing s is greater than a height $t_2$ of the flexible member 40 ($s/t_2>1$). The height $t_2$ of the flexible member 40 is the distance from the tip of the feet to the surface of the optical fiber embedment portion 41A. A width w of each of the feet 42 is less than the prescribed spacing s (w<s). In FIG. 16, the tips of the plurality of feet 42 contact the laminated sheet 12B. In the state where no pressure is applied, the plurality of feet 42 support the optical fiber embedment portion 41 so that a gap is formed between the optical fiber embedment portion 41B and the laminated sheet 12B.

As illustrated in FIG. 17, when pressure is applied to the bonded structure 21 from the vertical direction, those portions of the optical fiber embedment portion 41 and the distributed optical fiber 16 embedded therein that are positioned between the feet 42 warp. These warped portions contact the laminated sheet 12B, and the laminated sheet 12A and the laminated sheet 12B are bonded together. When the laminated sheet 12A and the laminated sheet 12B reach a bonded state and pressure is applied in the radial direction of the distributed optical fiber 16, the core of the distributed optical fiber 16 expands in the axial direction.

As a result, the bonded structure 21 according to the fifth embodiment can easily convert radial deformation in the distributed optical fiber 16 to axial deformation. This enables detection of the bonding state in the bonded structure 21. In the fifth embodiment, by setting the thickness $t_1$ of the optical fiber embedment portion 41, the thickness $t_2$ of the flexible member 40, the width w of the feet 42, and the spacing s between adjacent feet 42 so as to satisfy the size correlations described above, the flexible member 40 can be warped in a stable manner, enabling favorable detection of the bonding state in the bonded structure 21.

Figure 19:
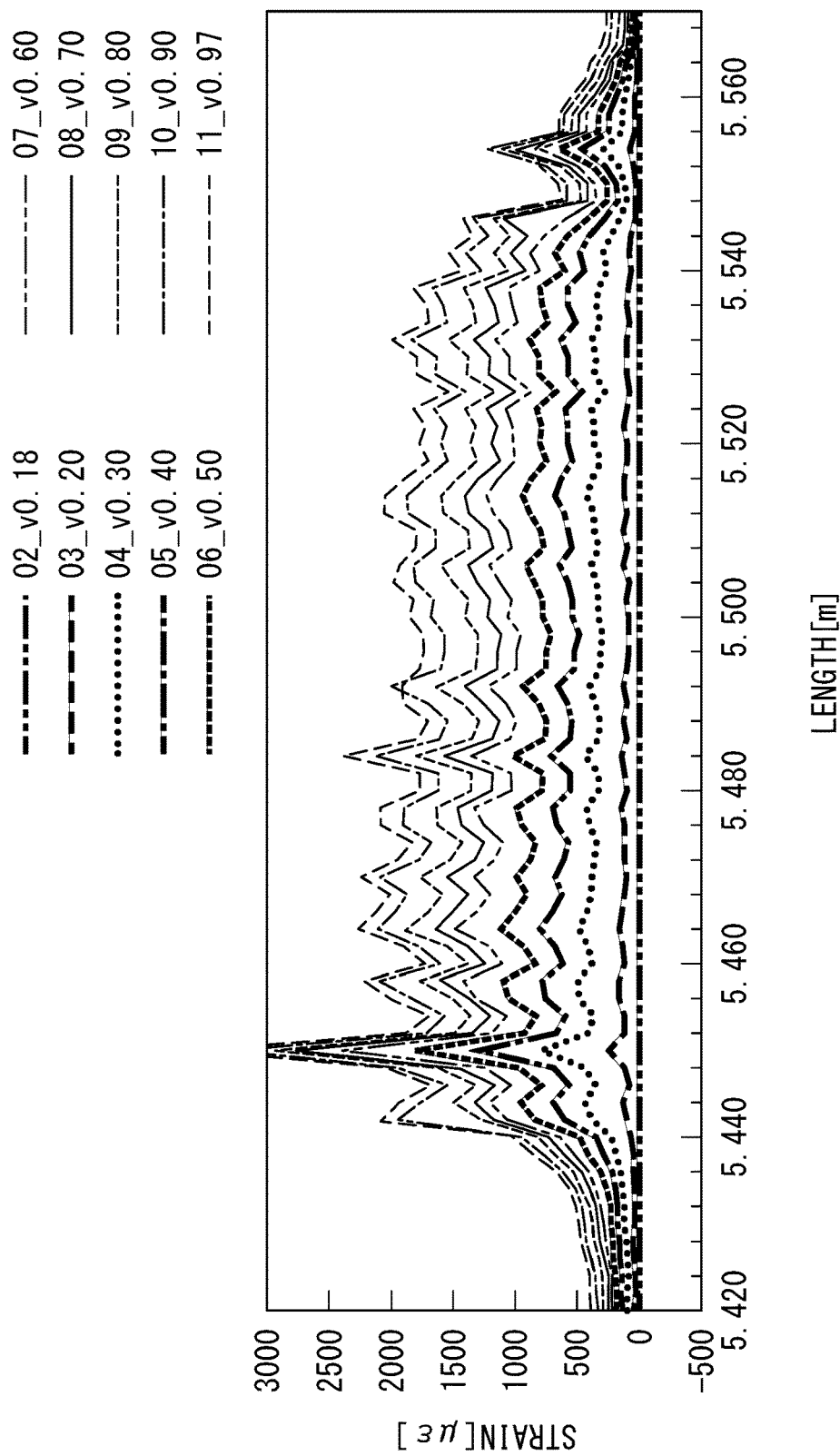
FIG. 19 A graph illustrating the test results for a bonded structure using a flexible member according to the fifth embodiment of the present invention.

FIG. 19 illustrates test results for the bonded structure 21 according to the fifth embodiment. The test piece was a bonded structure 21 in which the flexible member 40 containing the embedded distributed optical fiber 16 was sandwiched between laminated sheets 12A and 12B composed of aluminum sheets, with pressure than applied to this bonded structure 21 from the vertical direction.

The "Length (m)" shown along the horizontal axis of FIG. 19 represents the length of the distributed optical fiber 16, and indicates the position of pressure detection. The "Strain (με)" shown along the vertical axis of FIG. 19 is a value indicating the strain in the axial direction of the distributed optical fiber 16, wherein a positive value indicates an expansion and a negative value indicates a contraction.

In the test, the portion where pressure was applied to the bonded structure 21 (hereafter referred to as the "compressed portion") is from about 5.43 m to 5.56 m. The pressure applied to the bonded structure 21 in the test was within a range from 0.18 atm (about 0.018 MPa) to 0.97 atm (about 0.1 MPa).

In FIG. 19, when the pressure was 0.18 atm, there was no axial strain. The axial strain fluctuated by greater amounts as the pressure was increased.

Figure 20:
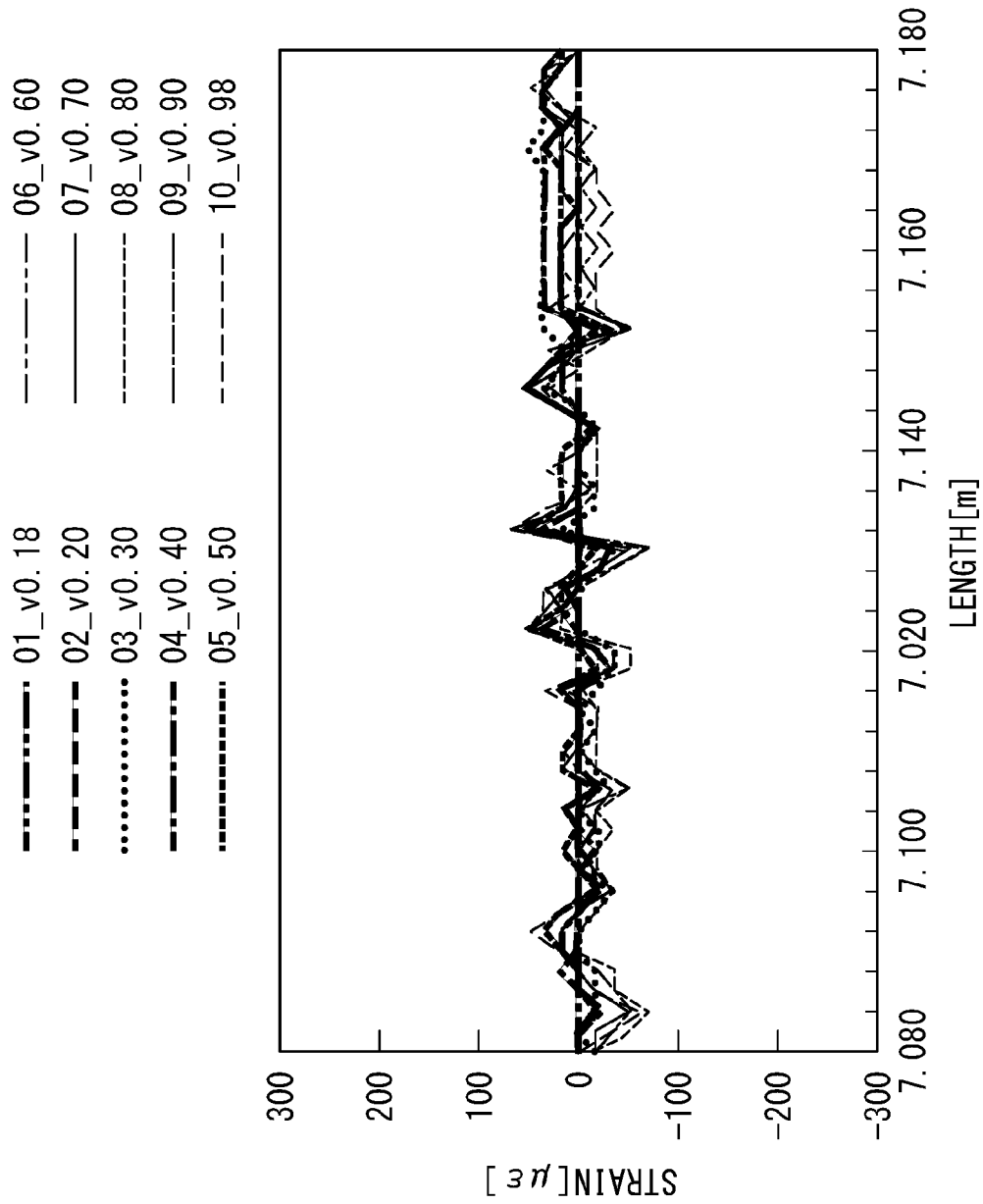
FIG. 20 A graph illustrating the test results for a bonded structure using a sensitivity improvement element according to the first embodiment of the present invention.

FIG. 20 illustrates test results for the bonded structure 10 according to the first embodiment. The test piece was the bonded structure 10 having the distributed optical fiber 16 sandwiched between the sensitivity improvement element 30 and the laminated sheets 12A and 12B, and pressure was applied from the vertical direction of the bonded structure 10. The distributed optical fiber 16 used was the same as that used in the tests of FIG. 19.

The "Length (m)" shown along the horizontal axis of FIG. 20 represents the length of the distributed optical fiber 16, and indicates the position of pressure detection. The "Strain (με) "shown along the vertical axis of FIG. 20 is a value indicating the strain in the axial direction of the distributed optical fiber 16, wherein a positive value indicates an expansion and a negative value indicates a contraction.

In the test, the portion where pressure was applied to the bonded structure 10 (hereafter referred to as the "compressed portion") is from about 7.052 m to 7.156 m.The pressure applied to the bonded structure 10 in the test was within a range from 0.18 atm (about 0.018 MPa) to 0.98 atm (about 0.1 MPa).

In FIG. 20, when the pressure was 0.18 atm, there was no axial strain. The axial strain increased as the pressure was increased.

As illustrated in FIG. 19 and FIG. 20, positive (or negative) axial strain occurred continuously in the compressed portion. As a result, it is evident that in both the bonded structure 10 of the first embodiment and the bonded structure 21 of the fifth embodiment, the bonding state is being detected continuously. Comparison of FIG. 19 and FIG. 20 reveals larger changes in the axial strain in FIG. 19. Based on these results, it is evident that the bonded structure 21 of the fifth embodiment exhibits superior pressure tracking properties to the bonded structure 10 of the first embodiment.

Although the present invention has been described above using the aforementioned embodiments, the technical scope of the present invention is in no way limited by the embodiments described above. Various modifications and improvements can be made to the above embodiments without departing from the features of the present invention, and all such modifications and improvements are also included within the technical scope of the invention. The above embodiments may also be combined as appropriate.

For example, each of the above embodiments was described using the case where the laminated sheets 12A and 12B of a carbon fiber composite material were used as the members to be bonded, but the present invention is not limited to such members, and the members to be bonded may be fiber-reinforced resin-based composite materials reinforced with glass fiber or the like, or metal materials such as aluminum alloys.

The bonded structure 10 according to the embodiments described above may also be used for repairing damaged composite material structures.

Figure 21:
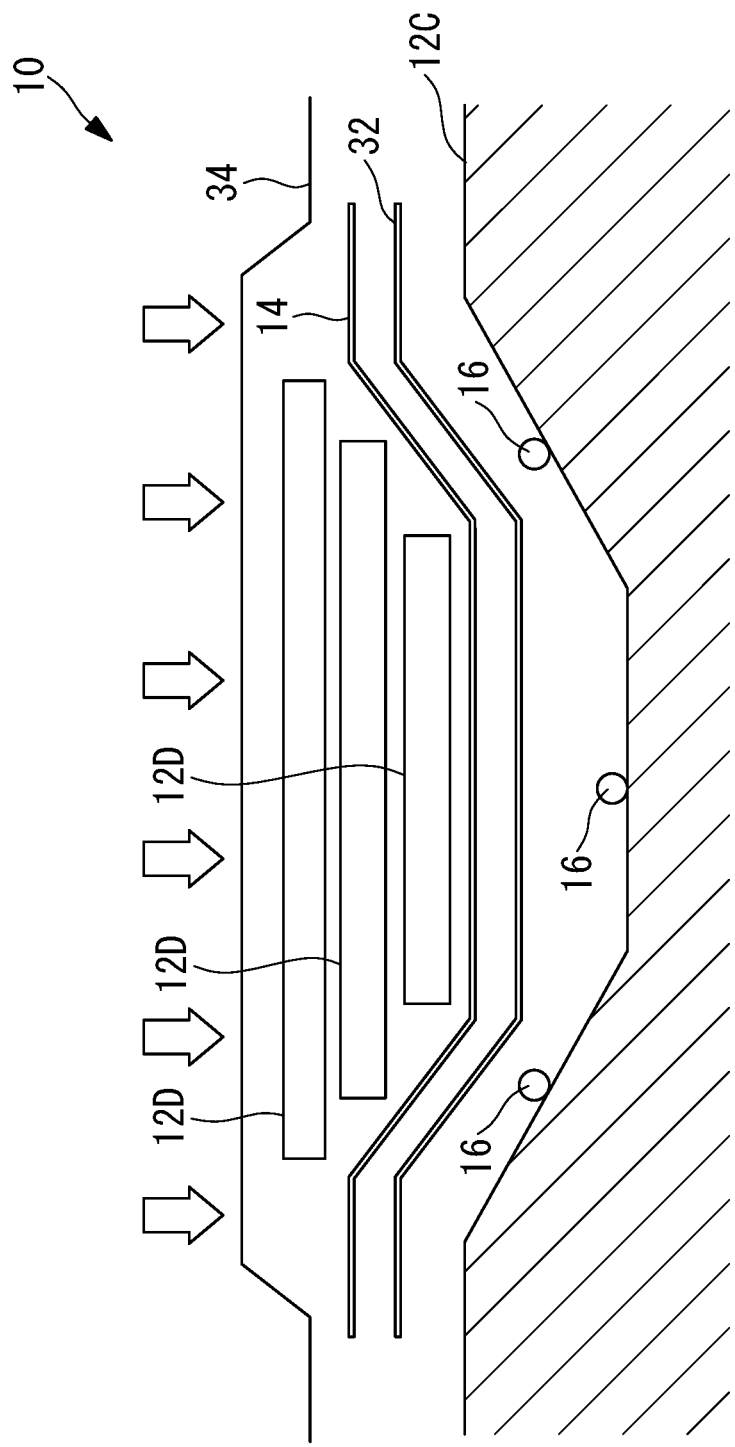
FIG. 21 A schematic view illustrating an example of a bonded structure according to another embodiment of the present invention.

FIG. 21 is a schematic view illustrating an example of a bonded structure 10 that can be used for repair. In the example illustrated in FIG. 21, the distributed optical fiber 16 is arranged so as to extend along the direction perpendicular to the surface of the paper.

As illustrated in FIG. 21, the distributed optical fiber 16 is arranged on a damaged laminated sheet 12C (item to be bonded) within a region requiring repair. Then, a release film 32 provided with a thermocouple, the adhesive 14, and a repair ply 12D that acts as the laminated sheet for repairing the region requiring repair are stacked on top of the distributed optical fiber 16. The region requiring repair is then covered with a bagging film 34, the structure is subjected to vacuum evacuation, and the region requiring repair is autoclaved.

Accordingly, during the autoclaving, the temperatures of the repair ply 12D and the laminated sheet 12C are measured by the thermocouple, and the pressure is measured by the distributed optical fiber 16. This enables confirmation to be made that the temperature and pressure for the repair are appropriate, namely that the autoclaving conditions are appropriate.

Once the autoclaving conditions have been confirmed as being appropriate, the release film 32 is peeled off, and the distributed optical fiber 16 is removed. The adhesive 14 and the repair ply 12D are then once again stacked in the region requiring repair, and following covering with the bagging film 34, autoclaving is performed under the confirmed appropriate conditions.

In this manner, by arranging the distributed optical fiber 16 on the laminated sheet 12C that requires repair, stacking the release film 32, the adhesive 14 and the repair ply 12D on top, and then applying pressure and using the distributed optical fiber 16 to detect the appropriateness of the pressure, the adequacy of the repair process can be evaluated, and a quality guarantee can be given for the repaired region.

An optical fiber according to the fourth embodiment described above may also be used as the distributed optical fiber 16. Further, an adhesive according to the second embodiment may be used as the adhesive 14. A structure according to the third embodiment may be used as the repair ply 12D. The sensitivity improvement element 30 according to the first embodiment may also be used.

Figure 22:
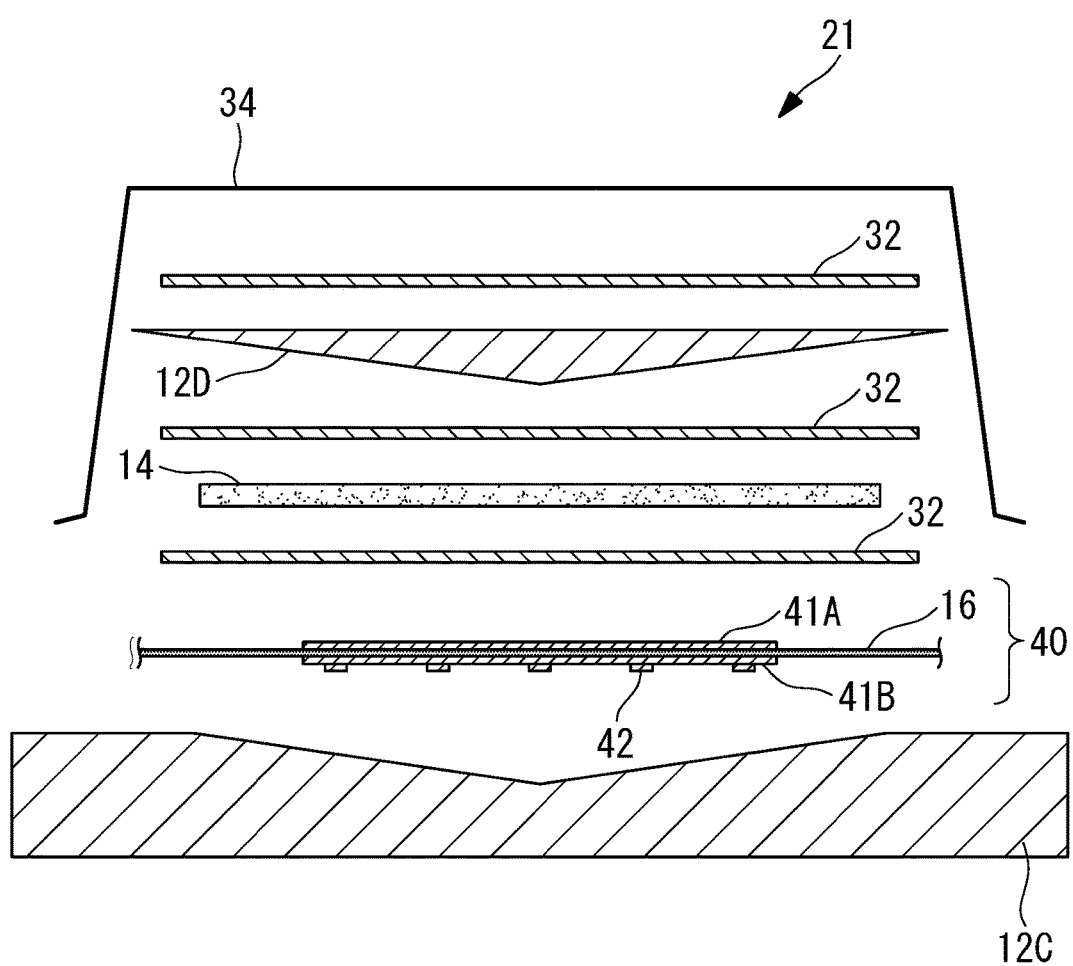
FIG. 22 A schematic view illustrating an example of a bonded structure according to yet another embodiment of the present invention.

FIG. 22 is a schematic view illustrating an example of a bonded structure 21 that can be used for repair. FIG. 22 illustrates the state prior to pressure application. In the example illustrated in FIG. 22, the distributed optical fiber 16 is arranged so as to extend left top right along the surface of the paper.

As illustrated in FIG. 22, the flexible member 40 containing the embedded distributed optical fiber 16 is arranged on the region requiring repair of the damaged laminated sheet 12C (item to be bonded). The adhesive 14 and the repair ply 12D used as the laminated sheet for repairing the region requiring repair are then stacked on top of the flexible member 40. A separate release film 32 is disposed between the flexible member 40 and the adhesive 14, between the adhesive 14 and the repair ply 12D, and on top of the repair ply 12D. The region requiring repair is then covered with a bagging film 34, and pressurized by vacuum evacuation or the like.

As a result, the pressure applied to the repair ply 12D and the laminated sheet 12C is measured by the distributed optical fiber 16. This enables confirmation to be made that the pressure for the repair is appropriate.

Once the pressure conditions for repair have been confirmed as being appropriate, the release films 32 are peeled off, and the flexible member 40 is removed. The adhesive 14 and the repair ply 12D are then once again stacked in the region requiring repair, and following covering with the bagging film 34, the repair is performed under the confirmed appropriate conditions.

In this manner, by arranging the distributed optical fiber 16 on the laminated sheet 12C that requires repair, stacking the release film 32, the adhesive 14 and the repair ply 12D on top, and then applying pressure and using the distributed optical fiber 16 to detect the appropriateness of the pressure, the adequacy of the repair process can be evaluated, and a quality guarantee can be given for the repaired region.

REFERENCE SIGNS LIST

10, 21: Bonded structure
12A: Laminated sheet
12B: Laminated sheet
12C: Laminated sheet
12D: Repair ply
14: Adhesive
16: Distributed optical fiber
16C: Core
16D: Cladding
20: Connector
30: Sensitivity improvement element
32: Release film
34: Bagging film
40: Flexible member
41A, B: Optical fiber embedment portion
42: Foot

The invention claimed is:

1. A bonded structure comprising:
   a first member,
   a second member,
   an adhesive that bonds the first member and the second member together, and
   a distributed optical fiber sandwiched between the first member and the second member and used as a pressure sensor that functions as a sensor along an entire length of the optical fiber in an axial direction thereof, wherein
   the distributed optical fiber is deformed in a radial direction in accordance with a bonding state between the first member and the second member,
   a radial deformation of the distributed optical fiber is converted into a contraction or expansion of the distributed optical fiber, and
   the bonding state along the axial direction of the distributed optical fiber is continuously detected by axial strain caused by the contraction or expansion of the distributed optical fiber along the axial direction.

2. The bonded structure according to claim 1, wherein the distributed optical fiber has a property of contracting or expanding when the first member and the second member reach a bonded state compared with a case where the first member and the second member are in an unbonded state.

3. The bonded structure according to claim 2, wherein when the first member and the second member are in an unbonded state, the distributed optical fiber is arranged in a wave-like shape relative to a lamination direction of the first member and the second member.

4. The bonded structure according to claim 3, wherein the distributed optical fiber is sandwiched between the first member and the second member via a wave-like member having a wave-like surface.

5. The bonded structure according to claim 3, wherein a surface of the adhesive that contacts the distributed optical fiber has a wave-like shape.

6. The bonded structure according to claim 3, wherein at least one of the first member and the second member has a wave-like surface that contacts the distributed optical fiber.

7. The bonded structure according to claim 2, wherein a cladding that coats a core of the distributed optical fiber is formed with repeating large diameter sections and small diameter sections.

8. The bonded structure according to claim 3, wherein
the distributed optical fiber is sandwiched between the first member and the second member in a state embedded in a flexible member,
the flexible member has an optical fiber embedment portion in which the distributed optical fiber is embedded, and a plurality of feet protruding from the optical fiber embedment portion, and
the plurality of feet are arranged with spaces therebetween.

9. A method for manufacturing a bonded structure, the method comprising:
a step of applying an adhesive to at least one of a first member and a second member, and
a step of sandwiching a distributed optical fiber used as a pressure sensor, which functions as a sensor along an entire length of the optical fiber in an axial direction thereof, between the first member and the second member to which the adhesive has been applied such that the distributed optical fiber is deformed in a radial direction in accordance with a bonding state between the first member and the second member and a radial deformation of the distributed optical fiber is converted into a contraction or expansion of the distributed optical fiber which allows detection of the bonding state continuously along the axial direction of the distributed optical fiber, and applying pressure, thereby causing axial strain by the contraction or expansion of the distributed optical fiber in the axial direction, and bonding the first member and the second member together.

10. The method for manufacturing a bonded structure according to claim 9, wherein a radial deformation in the distributed optical fiber that occurs as a result of the pressure application is converted to an axial deformation, and a bonding state between the first member and the second member is detected based on the axial deformation.

11. The method for manufacturing a bonded structure according to claim 9, wherein the distributed optical fiber is formed from a material that has a property of contracting or expanding when the first member and the second member reach a bonded state compared with a case where the first member and the second member are in an unbonded state.

12. The method for manufacturing a bonded structure according to claim 11, wherein when the first member and the second member are in an unbonded state, the distributed optical fiber is arranged in a wave-like shape relative to a direction of the first member and the second member.

13. The method for manufacturing a bonded structure according to claim 11, wherein the distributed optical fiber is sandwiched between the first member and the second member via a wave-like member having a wave-like surface.

14. The method for manufacturing a bonded structure according to claim 11, wherein a surface of the adhesive that contacts the distributed optical fiber has a wave-like shape.

15. The method for manufacturing a bonded structure according to claim 11, wherein at least one of the first member and the second member is formed with a wave-like surface that contacts the distributed optical fiber.

16. The method for manufacturing a bonded structure according to claim 11, wherein the distributed optical fiber is sandwiched between the first member and the second member via a flexible member having an optical fiber embedment portion in which the distributed optical fiber is embedded and a plurality of feet protruding from the optical fiber embedment portion and arranged with spaces therebetween.

17. A bonding state detection method comprising:
a first step of bonding a first member and a second member with an adhesive while sandwiching a distributed optical fiber used as a pressure sensor, which functions as a sensor along an entire length of the optical fiber in an axial direction thereof, between the first and second members such that the distributed optical fiber is deformed in a radial direction in accordance with a bonding state between the first member and the second member and a radial deformation of the distributed optical fiber is converted into a contraction or expansion of the distributed optical fiber, and
a second step of detecting the bonding state between the first member and the second member continuously along the axial direction of the distributed optical fiber, the detecting being based on axial strain caused by the contraction or expansion of the distributed optical fiber converted from the radial deformation in the distributed optical fiber.

18. The bonding state detection method according to claim 17, wherein the distributed optical fiber is arranged on the first member, a release film, the adhesive and the second member are then stacked thereon and pressure is applied, and an appropriateness of the pressure is detected by the distributed optical fiber.

* * * * *